(12) United States Patent
Buller et al.

(10) Patent No.: US 11,591,626 B2
(45) Date of Patent: Feb. 28, 2023

(54) ENGINEERED BIOCATALYSTS FOR THE SYNTHESIS OF GAMMA-HYDROXY AMINO ACIDS

(71) Applicant: Wisconsin Alumni Research Foundation, Madison, WI (US)

(72) Inventors: Andrew R. Buller, Madison, WI (US); Jonathan M. Ellis, Madison, WI (US); Prasanth Kumar, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 8 days.

(21) Appl. No.: 17/072,472

(22) Filed: Oct. 16, 2020

(65) Prior Publication Data

US 2021/0115480 A1   Apr. 22, 2021

Related U.S. Application Data

(60) Provisional application No. 62/923,083, filed on Oct. 18, 2019.

(51) Int. Cl.
  *C12P 13/12* (2006.01)
  *C12N 9/10* (2006.01)

(52) U.S. Cl.
  CPC ............... *C12P 13/12* (2013.01); *C12N 9/13* (2013.01)

(58) Field of Classification Search
  CPC . C12P 13/12; C12P 13/04; C12N 9/13; C12N 9/88; C12Y 401/01
  See application file for complete search history.

(56) References Cited

PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Altschul et al., "Gapped BLAST and PSI-BLAST: a new generation of protein database search programs," *Nucleic Acids Res.* 25:3389-3402, 1997.
Blaskovich, M. A. T. "Unusual Amino Acids in Medicinal Chemistry," *Journal of Medicinal Chemistry* 59, 10807-10836, 2016.
Devereux et al., A comprehensive set of sequence analysis programs for the VAX, *Nucl. Acid Res.*, 12:387-395, 1984.
Godfrey, A. G., Masquelin, T. & Hemmerle, H. "A remote-controlled adaptive medchem lab: an innovative approach to enable drug discovery in the 21st Century," *Drug Discovery Today* 18, 795-802, 2013.

(Continued)

*Primary Examiner* — Iqbal H Chowdhury
(74) *Attorney, Agent, or Firm* — Joseph T. Leone; DeWitt LLP

(57) ABSTRACT

A DNA expression construct comprising a polynucleotide encoding an unnatural UstD enzyme, the unnatural enzyme itself, and a method of making gamma-hydroxy amino acids by contacting an aldehyde-containing substrate, an amino acid, and the unnatural, purified UstD enzyme under conditions and for a time sufficient to react at least a portion of the aldehyde-containing substrate with at least a portion of the amino acid, to yield a gamma-hydroxy amino acid product.

14 Claims, 16 Drawing Sheets

Figure 1:
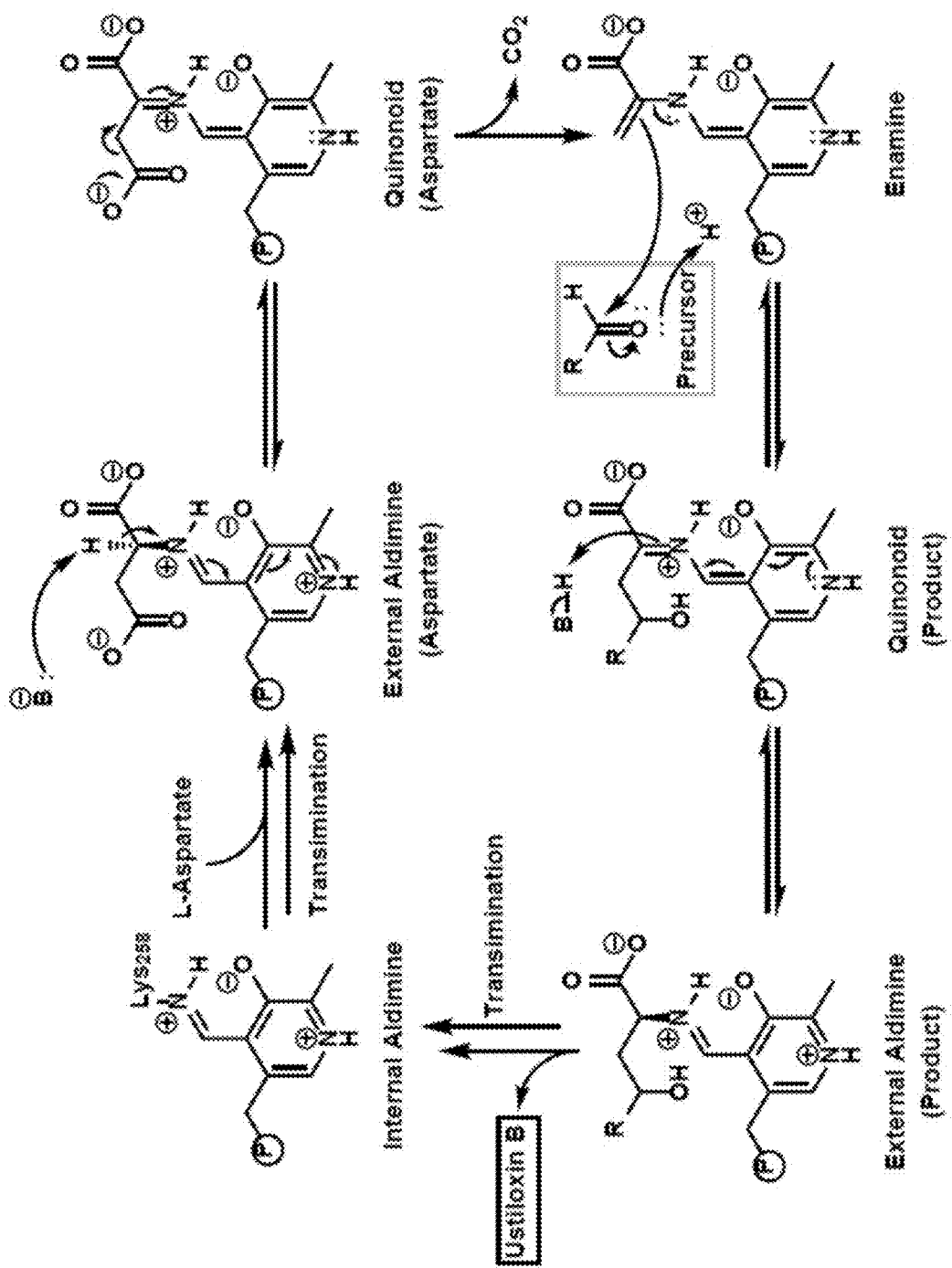
Figure 2:
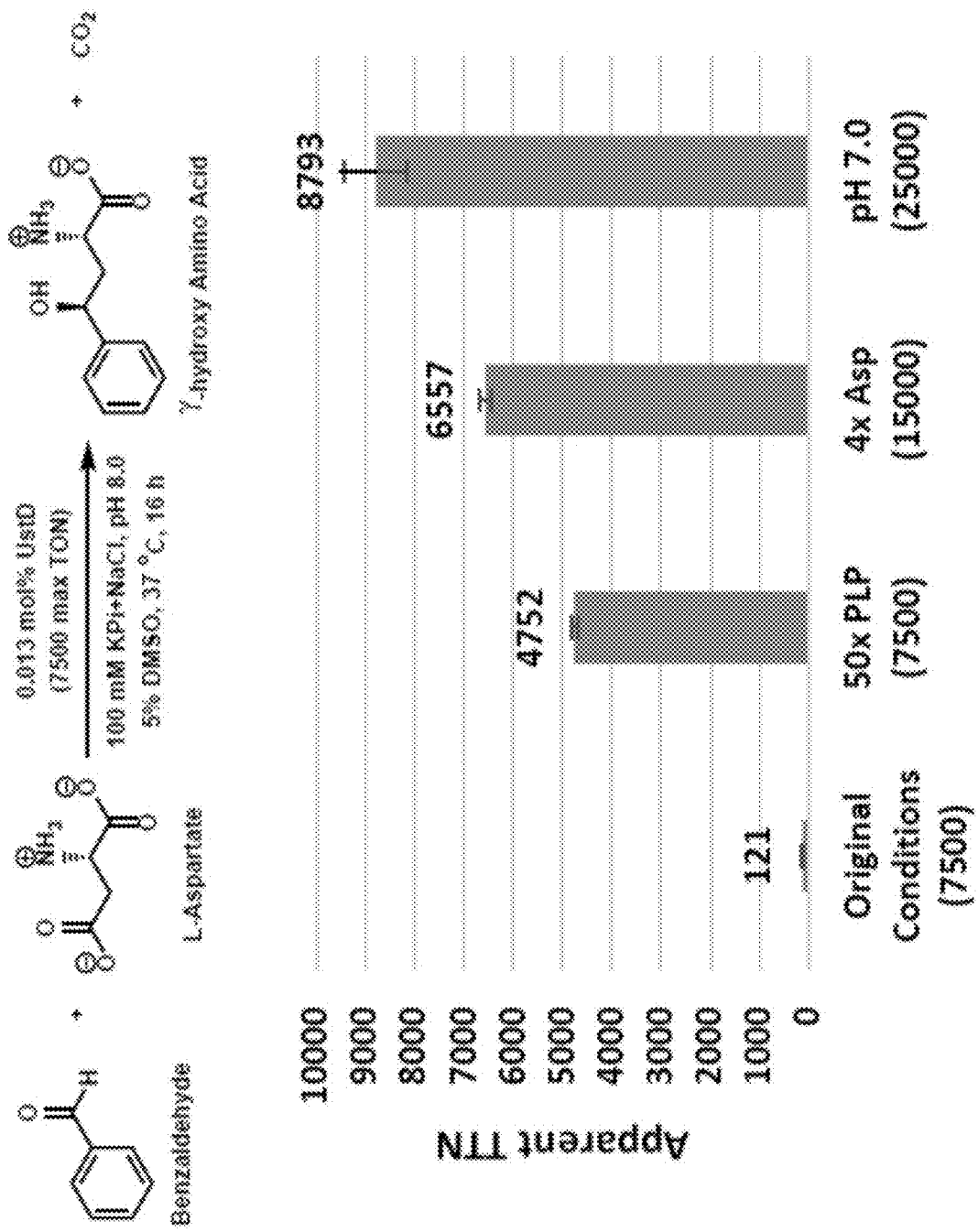

Specification includes a Sequence Listing.

(56) References Cited

PUBLICATIONS

Guex, N., Peitsch, M. C. & Schwede, T. "Automated comparative protein structure modeling with Swiss-Model and Swiss-PdbViewer: A historical perspective," *Electrophoresis* 30, S162-S173, 2009.

Károly Micskei, Patonay, T., Caglioti, L. & Palyi, G. "Amino Acid Ligand Chirality for Enantioselective Syntheses," *Chemistry & Biodiversity*, 7, 6, 1660-1669, 2010.

Kille et al. Reducing Codon Redundancy and Screening Effort of Combinatorial Protein Libraries Created by Saturation Mutagenesis, *ACS Synth. Biol.* 2013, 2, 2, 83-92, Jun. 15, 2012.

Needleman and Wunsch, A General Method Application to the Search for Similarities in the Amino Acid Sequence of Two Proteins, *J. Mol. Biol.*, 48:443, 1970.

Notredame et al., "T-Coffee: A novel method for multiple sequence alignments," *Journal of Molecular Biology* 302: 205-217, 2000.

Pearson and Lipman, Improved tools for biological sequence comparison, *Proc. Natl. Acad. Sci. USA* 85:2444, 1988.

Roy, A., Kucukural, A. & Zhang, Y. "I-TASSER: a unified platform for automated protein structure and function prediction," *Nat. Protoc.* 5, 725-738, 2010.

Smith and Waterman, Comparison of Bioisequences, *Adv. Appl. Math.*, 2:482, 1981.

Thompson J. D., Higgins D. G., Gibson T. J., "Clustal W: improving the sensitivity of progressive multiple sequence alignment through sequence weighting, position-specific gap penalties and weight matrix choice," *Nucleic Acids Research* 22: 4673-4680, 1994.

Umemura, M. et al. "Characterization of the biosynthetic gene cluster for the ribosomally synthesized cyclic peptide ustiloxin B in *Aspergillus flavus*," *Fungal Genet. Biol.* 68, 23-30, 2014.

Waterhouse, A. et al. "Swiss-Model: homology modelling of protein structures and complexes," *Nucleic Acids Res.* 46, W296-W303, 2018.

Yang, J. et al. "The I-TASSER Suite: protein structure and function prediction," *Nat. Methods* 12, 7-8, 2015.

Ye, Y. et al. "Unveiling the Biosynthetic Pathway of the Ribosomally Synthesized and Post-translationally Modified Peptide Ustiloxin B in Filamentous Fungi," *Angew. Chemie—Int. Ed.* 55, 8072-8075, 2016.

Zhang, Y., Farrants, H. & Li, X. "Adding a Functional Handle to Nature's Building Blocks: The Asymmetric Synthesis of b-Hydroxy-a-Amino Acids," *Chem. Asian J* 9, 1752-1764, 2014.

\* cited by examiner

ENGINEERED BIOCATALYSTS FOR THE SYNTHESIS OF GAMMA-HYDROXY AMINO ACIDS

CROSS-REFERENCE TO RELATED APPLICATIONS

Priority is hereby claimed to provisional application Ser. No. 62/923,083, filed Oct. 18, 2019, which is incorporated herein.

BACKGROUND

Amino acids are among the premier building blocks of nature, ranging in use from protein production to secondary metabolite generation. For chemists, amino acids act as a core chiral reagent pool for making a wide variety of important molecules, such as chiral ligands for catalysis and starting materials for diverse syntheses. See, for example, Károly Micskei, Patonay, T., Caglioti, L. & Pályi, G. "Amino Acid Ligand Chirality for Enantioselective Syntheses," *Chemistry & Biodiversity*, 7, 6, 1660-1669 (2010) and Zhang, Y., Farrants, H. & Li, X. "Adding a Functional Handle to Nature's Building Blocks: The Asymmetric Synthesis of b-Hydroxy-a-Amino Acids," *Chem. Asian J* 9, 1752-1764 (2014). Many natural products and clinically used drug molecules bear non-standard amino acids (nsAAs); nsAAs are amino acids that have been chemically modified via reactions such as halogenation, hydroxylation, alkylation, and cyclization. See Blaskovich, M. A. T. "Unusual Amino Acids in Medicinal Chemistry," *Journal of Medicinal Chemistry* 59, 10807-10836 (2016). These modifications may impart improved binding affinity, specificity, bioavailability, and stability to the compound. Diverse pools of novel nsAAs represent a key resource for high-throughput screening to find new drug candidates. See Godfrey, A. G., Masquelin, T. & Hemmerle, H. "A remote-controlled adaptive medchem lab: an innovative approach to enable drug discovery in the 21st Century," *Drug Discovery Today* 18, 795-802 (2013). Syntheses of nsAAs, however, is often a time-consuming and tedious process involving multiple chemical transformations and purifications.

By studying the biosynthetic pathways of natural products bearing nsAAs, it is possible to discover how a given organism can make nsAAs in vivo. These nsAA-containing biosynthesis pathways generally fall into two categories; a first pathway in which the nsAA is synthesized and then incorporated into the natural product of interest, and a second pathway in which a natural product core scaffold is formed and subsequently modified to contain one or more nsAAs. Both routes typically involve highly specialized enzymes to carry out the transformations. These enzymes have evolved to perform diverse chemo-, stereo-, and regioselective transformations. Many of these transformations are extremely challenging to accomplish via traditional synthetic chemistry.

Recently, the biosynthetic pathway of Ustiloxin B, a fungal ribosomally synthesized and post-translationally modified peptide (RiPP) from *Aspergillus flavus*, was characterized. (Umemura, M. et al. "Characterization of the biosynthetic gene cluster for the ribosomally synthesized cyclic peptide ustiloxin B in *Aspergillus flavus*," *Fungal Genet. Biol.* 68, 23-30 (2014). Ye, Y. et al. "Unveiling the Biosynthetic Pathway of the Ribosomally Synthesized and Post-translationally Modified Peptide Ustiloxin B in Filamentous Fungi," *Angew. Chemie—Int. Ed.* 55, 8072-8075 (2016).) The final step of the biosynthetic pathway involves a pyridoxal 5'-phosphate (PLP)-dependent enzyme: UstD. This enzyme catalyzes the decarboxylation of L-aspartate to form a nucleophilic enamine intermediate. See FIG. 1, which illustrates the proposed mechanism. Instead of protonation of the enamine to form L-alanine, as is the case with L-aspartate β-decarboxylases, UstD catalyzes addition of the enamine into an aldehyde moiety of the precursor to Ustiloxin B.

SUMMARY

As described herein, the decarboxylative, aldol-like reactivity of UstD has been harnessed to implement a method for directly converting aldehyde-bearing molecules into gamma-hydroxy amino acids. Thus, disclosed herein is a method of using UstD and its homologs as synthetic biocatalysts to produce a wide variety of gamma-hydroxy amino acids. More specifically, disclosed herein is a method of making a gamma-hydroxy amino acid. The method comprises contacting an aldehyde-containing substrate, an amino acid, and an unnatural, mutated UstD enzyme having at least 50% sequence identity but less than 100% sequence identity to a wild-type UstD enzyme as shown in SEQ. ID. NO: 1, under conditions and for a time sufficient to react at least a portion of the aldehyde-containing substrate with at least a portion of the amino acid, to yield a gamma-hydroxy amino acid product. The unnatural, mutated UstD enzyme may have at least 60%, at least 70%, at least 80%, at least 90%, or at least 95%, sequence identity but less than 100% with the amino acid sequence of SEQ. ID. NO: 1.

In one version of the method, the aldehyde-containing substrate is present at a given concentration and the amino acid is present at a concentration at least 4-fold higher than the concentration of the aldehyde-containing substrate. The aldehyde-containing substrate may also be present at a concentration at least 10-fold higher than the concentration of the aldehyde-containing substrate.

In another version of the method, the aldehyde-containing substrate, the amino acid, and the unnatural, mutated UstD enzyme, are contacted in the presence of pyridoxal 5'-phosphate. In this version of the method, the aldehyde-containing substrate may be present at a given concentration and the amino acid is present at a concentration at least 4-fold higher than the concentration of the aldehyde-containing substrate, and preferably at least 10-fold higher than the concentration of the aldehyde-containing substrate. The unnatural, mutated UstD enzyme may present at a given concentration and the pyridoxal 5'-phosphate is present at a concentration at least 20-fold higher or at least 40-fold higher than the concentration of the unnatural, mutated UstD enzyme.

In all versions of the method, the unnatural, mutated UstD enzyme may comprise an amino acid sequence as shown in SEQ. ID. NO: 1, wherein at least one residue selected from positions 122, 139, 227, 236, and 428, is not cysteine.

In all versions of the method, the unnatural, mutated UstD enzyme may comprise an amino acid sequence selected from the group consisting of SEQ. ID. NOS: 4, 5, 6, 7, 8, 9, 10, 11, 12, and 13.

Also disclosed herein is an unnatural, mutated UstD enzyme having at least 50% sequence identity but less than 100% sequence identity to a wild-type UstD enzyme as shown in SEQ. ID. NO: 1. The unnatural, mutated UstD enzyme may comprise an amino acid sequence as shown in SEQ. ID. NO: 1, wherein at least one residue selected from positions 122, 139, 227, 236, and 428, is not cysteine. The unnatural, mutated UstD enzyme may comprise an unnatural, mutated UstD enzyme selected from the group consisting of SEQ. ID. NOS: 4, 5, 6, 7, 8, 9, 10, 11, 12, and 13.

Also disclosed herein is an unnatural, isolated polynucleotide encoding an unnatural, mutated UstD enzyme having at least 50% sequence identity but less than 100% sequence identity to a wild-type UstD enzyme as shown in SEQ. ID. NO: 1.

Further disclosed herein is a DNA expression construct comprising a polynucleotide encoding an unnatural, mutated UstD enzyme having at least 50% sequence identity but less than 100% sequence identity to a wild-type UstD enzyme as shown in SEQ. ID. NO: 1 and further comprising regulatory polynucleotides operationally linked to, and configured to, drive expression of the encoded unnatural, mutated UstD enzyme in a host cell transformed to contain the DNA expression construct.

BRIEF DESCRIPTION OF THE DRAWINGS

FIG. 1 depicts a proposed mechanism of action for the enzyme UstD.

FIG. 2 is a scheme depicting a screening reaction for condition optimization and original reaction conditions. The histogram depicts a summary of iterative reaction condition optimization for UstD. Bar labels indicate change in conditions from previous iteration. Average apparent total turnover number (TTN) for each step is indicated above each bar. Maximum turnover number (TON) for a given step is given in parenthesis below the varied condition label. (See also FIGS. 6A, 6B, and 6C.)

FIG. 3 is a histogram depicting the increase in TTN of UstD through multiple rounds of mutagenesis. Values above the bar graph represent TTN observed (triplicate pending) for a given variant. The superscripts in the labels for each bar represent the UstD mutant used—i.e., how the UstD variant was mutagenized in region (I391-C392-L393) with respect to the wild-type sequence.

FIG. 4 shows non-limiting examples of suitable substrates for UstD. UstDWT was used for reactions. TTN values were calculated based on apparent conversion method, except for glycolaldehyde and pyruvate where comparison of reactions at two separate catalyst loadings followed by estimation was used.

FIG. 5A is a histogram depicting TTN for a variety of substrates. The aldehyde starting material for each reaction set is indicated. Reactions were conducted in parallel using the optimized reaction conditions described above. The figure demonstrates the general nature of the method disclosed herein and variant performance.

FIG. 5B depicts a histogram as in FIG. 5A using glycolaldehyde as the substrate. Here, unreacted starting material was not quantifiable, so the relative MS peak area (positive mode, 150 m/z) of the product as compared to wild-type is shown.

FIG. 6A is a graph depicting the apparent total turnover number (TTN) of the subject method as a function of PLP concentration.

FIG. 6B is a graph depicting the apparent total turnover number (TTN) of the subject method as a function of L-aspartate concentration.

FIG. 6C is a graph depicting the apparent total turnover number (TTN) of the subject method as a function of initial reaction pH.

FIG. 7 is a rendering of a homology model of the UstD active site with simulated docking of 4-bromo-γ-hydroxy-homo-1-phenylalanine (gray) to PLP cofactor (yellow). Residue H148 is shown in magenta, and the four (4) residues mutagenized in the final saturation mutagenesis library are shown in cyan.

FIG. 8 is a representative sampling of various gamma-hydroxy amino acid products that have been made using the method disclosed herein. For all products, a product with the correct m/z was observed via UPLC-MS; no corresponding peak was observed in a no-enzyme (negative) control. Products in blue have been scaled to preparative levels. (See Examples section, below.) The structures of the compounds prepared at preparative scale have been confirmed by high-resolution MS and NMR to be diastereomerically pure.

FIG. 9 is a thermal ellipsoid crystal structure of 4-bromo-gamma-hydroxy-homo-L-phenylalanine. The structure confirms the conserved absolute configuration of stereocenters as compared to the native Ustiloxin B product.

FIG. 10 is an expanded proposed mechanism of UstD. The orange and red paths indicate shunt pathways. The pink and blue paths represent alternative on-path cycles.

FIGS. 11A, 11B, 11C, and 11D are histograms depicting turnover numbers of UstD through evolutionary trajectory on four different substrates. Dots represent individual measured values, bars represent average values of the dots for a given variant. All values were calculated using apparent conversion except for glycolaldehyde (FIG. 11D), which is calculated as the fold-product area against the average $UstD^{WT}$ area across the triplicate dataset. FIG. 11A depicts the results for benzaldehyde. FIG. 11B depicts the results for 4-biphenyl-carboxaldehyde. FIG. 11C depicts the results for 4-anisaldehyde. FIG. 11D depicts the results for glycoaldehyde.

DETAILED DESCRIPTION

Abbreviations and Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the term or value so referenced.

The term "alignment" refers to a method of comparing two or more polynucleotides or polypeptide sequences for the purpose of determining their relationship to each other. Alignments are typically performed by computer programs that apply various algorithms. It is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., "CLUSTAL W: improving the sensitivity of progressive multiple sequence alignment through sequence weighting, position-specific gap penalties and weight matrix choice," *Nucleic Acids Research* 22: 4673-4680, 1994); CLUSTALV, (see, Larkin M. A., et al., CLUSTALW2, "ClustalW and ClustalX version 2," *Bioinformatics* 23(21): 2947-2948, 2007); Jotun-Hein, Muscle et al., "MUSCLE: a multiple sequence alignment method with reduced time and space complexity," *BMC Bioinformatics* 5: 113, 2004); Mafft, Kalign, ProbCons, and T-Coffee (see Notredame et al., "T-Coffee: A novel method for multiple sequence alignments," *Journal of Molecular Biology* 302: 205-217, 2000). Exemplary programs that implement one or more of the above algorithms include, but are not limited to MegAlign from DNAStar (DNAStar, Inc. Madison, Wis., USA), MUSCLE, T-Coffee, CLUSTALX, CLUSTALV, JalView, Phylip, and Discovery Studio from Accelrys (Accelrys, Inc., San Diego, Calif., USA). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

BEH=bridged ethylene hybrid.

The term "contacting" refers to the act of touching, making contact, or of bringing to immediate or close proximity, including at the molecular level, for example, to bring about a chemical reaction, or a physical change, e.g., in a solution or in a reaction mixture.

DMSO=dimethylsulfoxide.

ESI=electro-spray ionization.

FMOC=fluorenylmethyloxycarbonyl chloride.

"Gene" refers to a polynucleotide (e.g., a DNA segment), which encodes a polypeptide, and includes regions preceding and following the coding regions as well as intervening sequences (introns) between individual coding segments (exons).

The term "homologous genes" refers to a pair of genes from different but related species, which correspond to each other and which are identical or similar to each other. The term encompasses genes that are separated by the speciation process during the development of new species (orthologous genes), as well as genes that have been separated by genetic duplication (paralogous genes).

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In certain versions of the genes and proteins described herein, homologous sequences can retain the same type and/or level of a particular activity of interest. In some versions, homologous sequences have between 85% and 100% sequence identity, whereas in other versions there is between 90% and 100% sequence identity. In particular embodiments, there is between 95% and 100% sequence identity.

"Homology" refers to sequence similarity or sequence identity. Homology is determined using standard techniques known in the art. (See, for example, Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA* 85:2444, 1988. See also programs such as GAP, BESTFIT, FASTA, and TFASTA in the Wisconsin Genetics Software Package (Genetics Computer Group, Madison, Wis., USA); and Devereux et al., *Nucl. Acid Res.*, 12:387-395, 1984.) A non-limiting example includes the use of the BLAST program (Altschul et al., "Gapped BLAST and PSI-BLAST: a new generation of protein database search programs," *Nucleic Acids Res.* 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The term "host strain" or "host cell" refers to a suitable host for an expression vector comprising a DNA of the present invention.

The term "hybridization" refers to the process by which a strand of polynucleotide joins with a complementary strand through base pairing, as known in the art. A polynucleotide sequence is "selectively hybridizable" to a reference polynucleotide sequence if the two sequences specifically hybridize to one another under moderate to high stringency hybridization and wash conditions. Hybridization conditions are based on the melting temperature ($T_m$) of the polynucleotide binding complex or probe. For example, "maximum stringency" typically occurs at about $T_m$–5° C. (that is, 5° C. below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or a low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/mL denatured carrier DNA followed by washing two times in 2×SSC and 0.5% SDS at room temperature and two additional times in 0.1×SSC and 0.5% SDS at 42° C. An example of moderate stringent conditions includes an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/mL denaturated sheared salmon sperm DNA, followed by washing the filters in 1×SSC at about 37° C. to about 50° C. Those of skill in the art know how to adjust the temperature, ionic strength, and other conditions as necessary to accommodate factors such as probe length and the like.

IPTG=Isopropyl β-D-1-thiogalactopyranoside.

The term "isolated" or "purified" means a material that is removed from its original environment, for example, the natural environment if it is naturally occurring, or a fermentation broth if it is produced in a recombinant host cell fermentation medium. A material is said to be "purified" when it is present in a composition in a higher or lower concentration than the concentration that exists prior to the purification step(s). For example, with respect to a composition normally found in a naturally occurring or wild type organism, such a composition is "purified" when the final composition does not include some material from the original matrix. As another example, where a composition is found in combination with other components in a recombinant host cell fermentation medium, that composition is purified when the fermentation medium is treated in a way to remove some component of the fermentation, for example, cell debris or other fermentation products through, for example, centrifugation or distillation. As another example, a naturally occurring polynucleotide or polypeptide present in a living animal is not isolated, but the same polynucleotide or polypeptide, separated from some or all of the coexisting materials in the natural system, is "isolated," whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

LOOCV=leave-one-out cross-validation.

NMR=nuclear magnetic resonance spectrometry.

nsAAs=non-standard amino acids.

The term "operationally linked" and "operably linked" are synonymous and, in the context of a polynucleotide sequence, refer to the placement of one polynucleotide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypeptide. A promoter or an enhancer is operably linked to a coding sequence if it affects the transcription of the sequence. A ribosome binding site is operably linked to a coding sequence if it is positioned to facilitate translation. "Operably linked" does not require that the DNA sequences so linked are contiguous (although that is often the case).

PDA=photodiode array.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

PLP=pyridoxal 5'-phosphate.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., Cl. F, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

TON=maximum turnover number.

TTN=apparent total turnover number.

TLC=Thin-layer chromatography

UPLC-MS=ultra-high-pressure liquid chromatography—mass spectrometry.

Numerical ranges as used herein are intended to include every number and subset of numbers contained within that range, whether specifically disclosed or not. That is, for all purposes, and particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

The methods of the present invention can comprise, consist of, or consist essentially of the essential elements and limitations of the method, molecules, and constructs described herein, as well as any additional or optional ingredients, components, or limitations described herein or otherwise useful in synthetic organic chemistry.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

Compounds disclosed herein may exhibit the phenomena of tautomerism, conformational isomerism, geometric isomerism and/or stereoisomerism. As the formula drawings within the specification and claims can represent only one of the possible tautomeric, conformational isomeric, stereochemical, or geometric isomeric forms, it should be understood that the present method encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

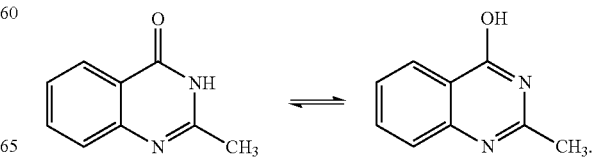

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used and made using the present method include enriched or resolved optical isomers at any or all asymmetric atoms as are apparent from the depictions (including enantiomers, diasteromers, and atropisomers). Racemic and diastereomeric mixtures, as well as the individual optical isomers can be enriched in any proportion or isolated or synthesized to be substantially free of their enantiomeric or diastereomeric partners, and these stereoisomers and atropisomers are all within the scope of the present disclosure.

All references to singular characteristics or limitations of the present invention shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage. For example, "one or more" substituents on a phenyl ring designates one to five substituents.

All combinations of method or process steps as used herein can be performed in any order, unless otherwise specified or clearly implied to the contrary by the context in which the referenced combination is made.

Figure 3:
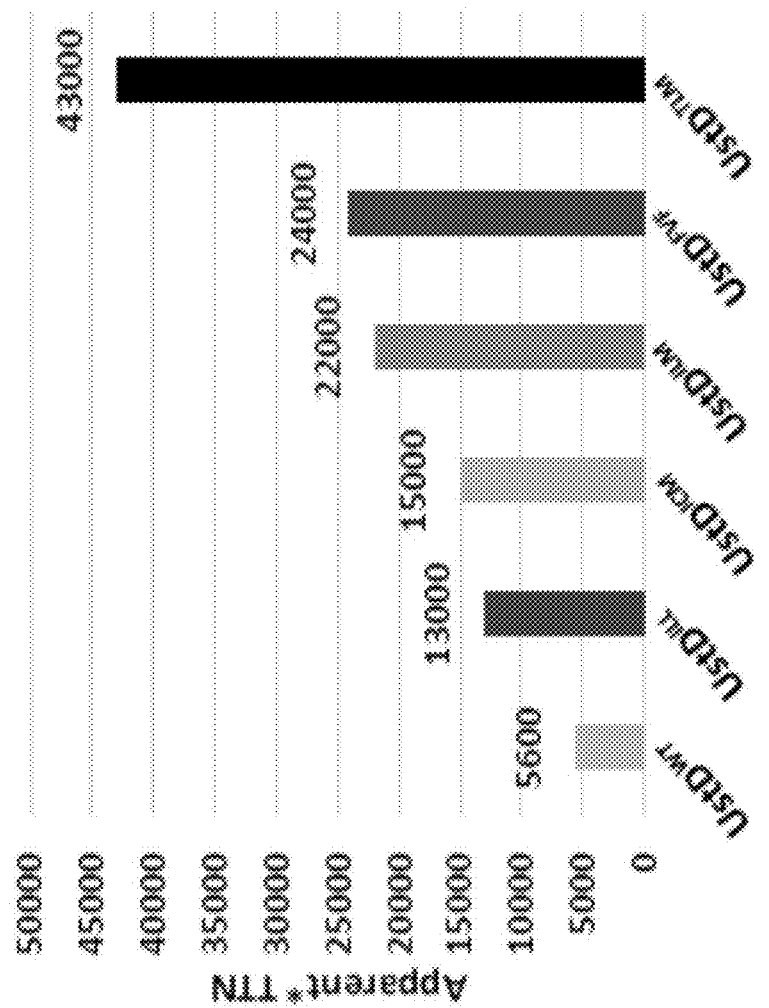

Expression and Characterization of UstD: A C-terminally 6× His-tagged, codon-optimized sequence of UstD from *A. flavus* was cloned into the IPTG controlled pET-22b(+) vector and transformed into BL21(DE3) *E. coli*. (New England BioLabs, Inc., Ipswich, Mass., USA, hereinafter "NEB"). Recombinant expression of UstD in Terrific Broth II ("TB") media (Thomas Scientific Swedesboro, N.J., USA) followed by harvest, lysis, and Ni-NTA affinity chromatography purification afforded a biocatalyst yield of ~8 mg/L TB. To test the activity of UstD, reactions were conducted using benzaldehyde as the target aldehyde starting material. This aldehyde was used as a general substrate for initial testing because the native Ustiloxin B precursor was not readily available. Product formation was assayed by UPLC-MS, and catalyst activity was calculated by dividing the product absorption peak area at 210 nm by the sum of the product and unreacted starting material peak area. This value was then multiplied by the maximum turnover number achievable for the given reaction to determine the apparent total turnover number (TTN). Under initial reaction conditions (see FIG. 2), UstD was able to catalyze the conversion of benzaldehyde to the corresponding y-hydroxy amino acid with a TTN of ~120. It was suspected that sub-optimal reaction conditions could be playing a role in the low catalytic activity, so a series of reaction condition optimization experiments were conducted.

To begin the optimization process, it was tested whether the presence of additional PLP in the reaction mixture affected the TTN of a reaction with 1:1 L-aspartate and benzaldehyde. It was reasoned that the PLP cofactor was potentially being destroyed during the reaction process because the catalytic reactions with benzaldehyde became colorless, while control reactions in the absence of enzyme remained yellow after 16 h. All reactions were done in triplicate to ensure consistency. A large boost in activity was observed with increasing concentrations of PLP, with an almost 40-fold increase in TTN at 50-fold PLP relative to UstD concentration. See FIG. 2, second bar from left. See also FIG. 6A. This large increase in TTN indicates that PLP was degraded during the reaction, though the precise origin of this degradation pathway is unknown.

Next, the amount of L-aspartate was varied to see if further improvements could be observed with the increased PLP concentration. A further doubling in TTN was observed at 10-fold aspartate relative to benzaldehyde concentration. (Data not shown; TTN data for 4-fold aspartate relative to benzaldehyde concentration is shown in FIG. 2, third bar from left.) See also FIG. 6B.

Finally, a pH profile was generated to find the optimal initial pH for reactivity. It was found that a pH of 7.0 provided an additional modest boost in activity, with the final optimized reaction conditions resulting in a maximum TTN of almost 8800. See FIG. 2, far right bar and FIG. 6C. These reaction conditions were used for all further preparative scale reactions with wild-type UstD. A similar optimization procedure can also be performed for variants of UstD to optimize yield.

Directed Evolution of UstD for Improved Catalytic Function:

With optimized reaction conditions in hand, efforts were shifted toward engineering UstD for improved activity. Methods used to screen UstD for activity are described in further detail in the examples below. Reaction conditions for screening were chosen to mimic idealized conditions, such as a 1:1 benzaldehyde:L-aspartate ratio for increased coupling efficiency. For the first round of engineering, a series of homology models of UstD was generated using the I-TASSER and SwissModel web services. See the following references Yang, J. et al. "The I-TASSER Suite: protein structure and function prediction," *Nat. Methods* 12, 7-8 (2015). Roy, A., Kucukural, A. & Zhang, Y. "I-TASSER: a unified platform for automated protein structure and function prediction," *Nat. Protoc.* 5, 725-738 (2010). Waterhouse, A. et al. "SWISS-MODEL: homology modelling of protein structures and complexes," *Nucleic Acids Res.* 46, W296-W303 (2018). Guex, N., Peitsch, M. C. & Schwede, T. "Automated comparative protein structure modeling with SWISS-MODEL and Swiss-PdbViewer: A historical perspective," *Electrophoresis* 30, S162-S173 (2009). See FIG. 7 for the resulting homology model. These models were used to guide targeting efforts for saturation mutagenesis of residues predicted to be near the putative active site of the enzyme. The model predicts that D232 is involved in hydrogen bonding to the pyridine nitrogen of the PLP cofactor. The protonation state of the pyridine nitrogen likely plays an important role in stabilizing the formed enamine intermediate. Thus mutations at D232 were expected to cause large changes in the activity of the enzyme. Indeed, all mutations observed at this position abolished activity of the biocatalyst. H148 was also predicted to be a it-stacking partner for the cofactor, and likely represents the residue which protonates the nascent oxyanion to form an alcohol in the product. While a small quantity of variants appeared to be moderately tolerated at this position, no variants led to an increase in activity. Four additional residues near the putative active site (A55, G84, Y257, C392) were also selected for saturation mutagenesis. Of these positions, one variant (C392L, $UstD^{ILL}$) was discovered with a 2.3-fold boost in observed activity relative to wild-type UstD ($UstD^{WT}$). See FIG. 3. In tandem with these saturation libraries, a global random mutagenesis library was generated. Serendipitously, an activated variant (L393M, UstD$^{ICM}$) was made and which displays a 2.7-fold boost in activity. The L393 residue neighbors the previously identified C392L position. It was hypothesized that these variants could exhibit a high degree of cooperativity when combined, and so the double variant (UstD$^{ILM}$) was generated. (Again, see FIG. 3.) Indeed, the double variant exhibited a 3.9-fold boost in activity relative to wild-type UstD. This seemed to indicate that this predicted loop region could be amiable to mutations and warranted further exploration.

A four-position degenerate-codon library including the residues which flank the C392 and L393 positions (I391, A394) was constructed to explore the mutational landscape of the region. Mutations resulting in primarily hydrophobic variants were selected, as the homology model predicted the putative loop region to be buried in the interior of the enzyme. For residue I391, a wide variety of possible variants were incorporated in the library to explore a diverse landscape. Residue A394 is predicted to be at the beginning of an alpha helix, so residues targeted towards exploring flexibility in the loop region were tested. Of note, mutations at C392 were chosen to omit the original residue identity. This was done in order to avoid the formation of cysteine sulfinic acid near the active site, which would result in potential heterogeneity in the biocatalyst state over the course of a reaction. A wide variety of activated variants were revealed using this targeted library, all of which retaining the identity of A394. Of the sequenced hits, two variants were chosen for further study, I391T-C392L-L393M (UstD$^{TLM}$) and I391F-C392V-L393F (UstD$^{FVF}$) UstD$^{TLM}$ represented the variant with the largest increase in activity observed during screening, while UstD$^{FVF}$ was chosen for its diversity in variant composition. It was determined that FVF bore a 4.3-fold boost in activity relative to wild-type UstD, while TLM resulted in a 7.7-fold boost. See FIG. 3.

Thus, as compared to the wild-type protein, these unnatural, mutated proteins have the following amino acid sequences:

C392L=UstD$^{ILL}$ SEQ. ID. NO: 4 (2.3× better than wt)
L393M=UstD$^{ICM}$ SEQ. ID. NO: 5 (2.7× better than wt)
C392L—L393M=UstD$^{TLM}$ SEQ. ID. NO: 6 (3.9× better than wt)
I391F-C392V-L393F=UstD$^{FVF}$ SEQ. ID. NO: 7 (4.3× better than wt)
I391T-C392L-L393M=UstD$^{TLM}$ SEQ. ID. NO: 8 (7.7× better than wt)

Figure 4:
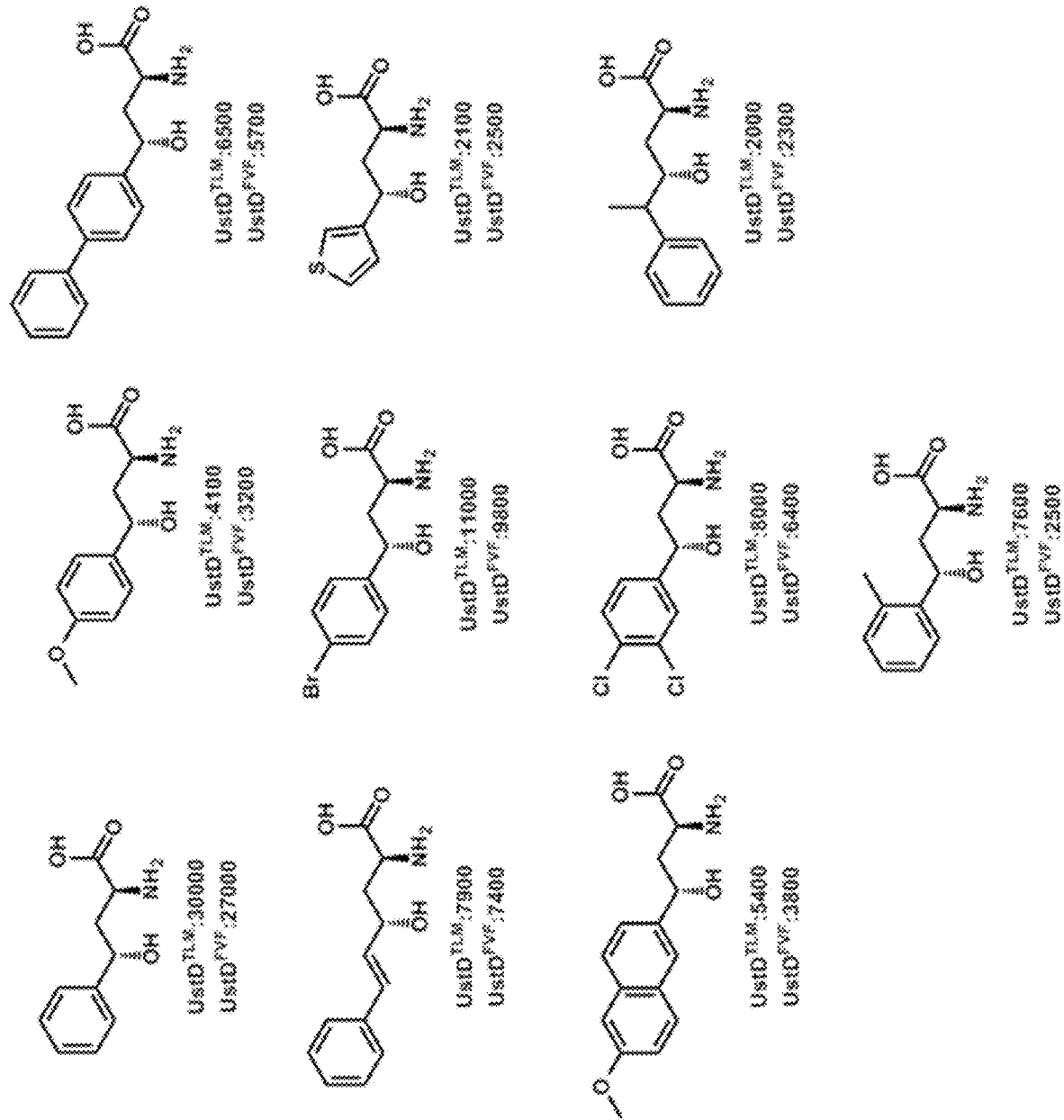
Figures 5A, 5B:
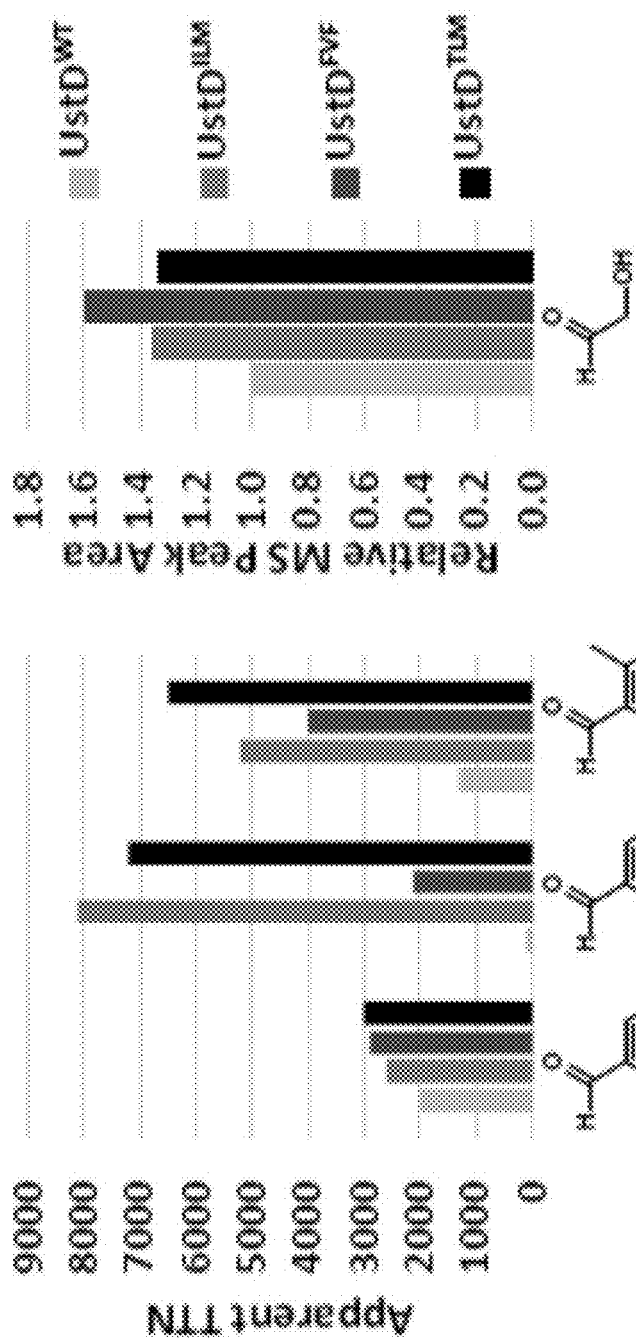
Figure 6A:
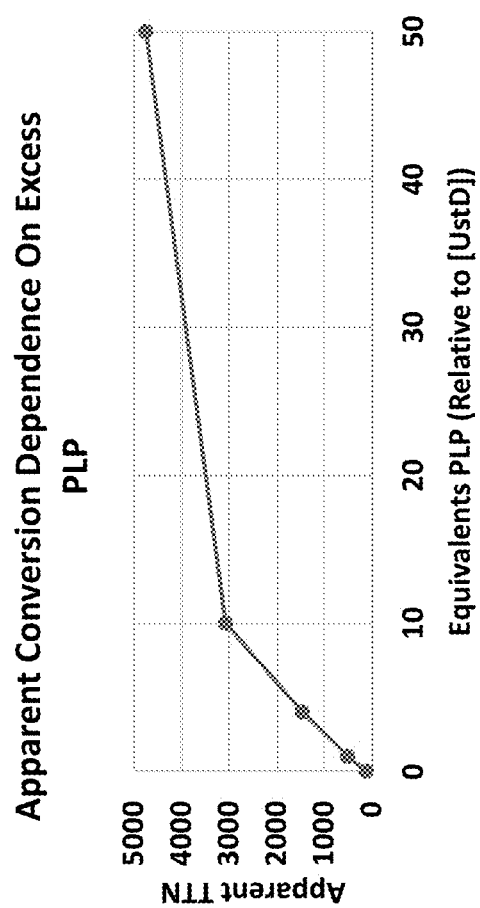
Figure 6B:
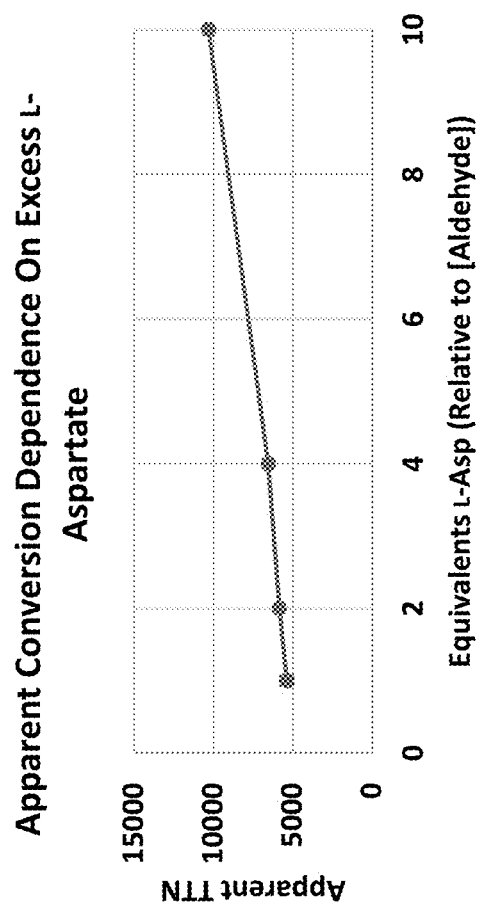
Figure 6C:
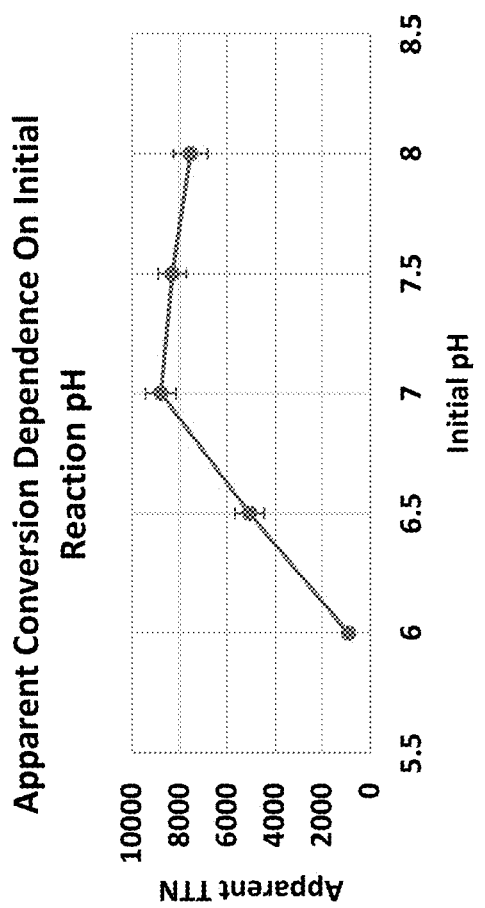
Figure 7:
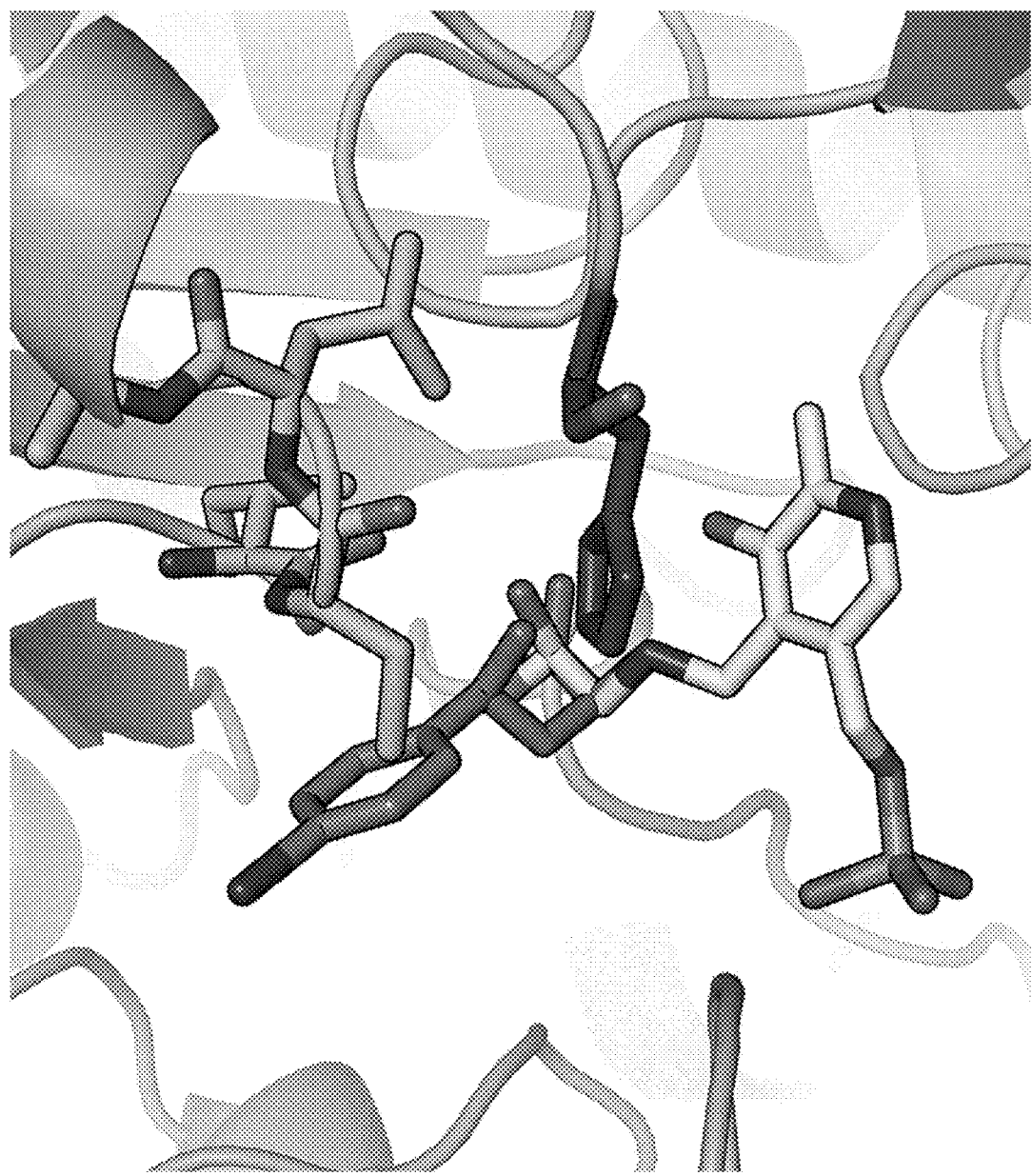
Figure 8:
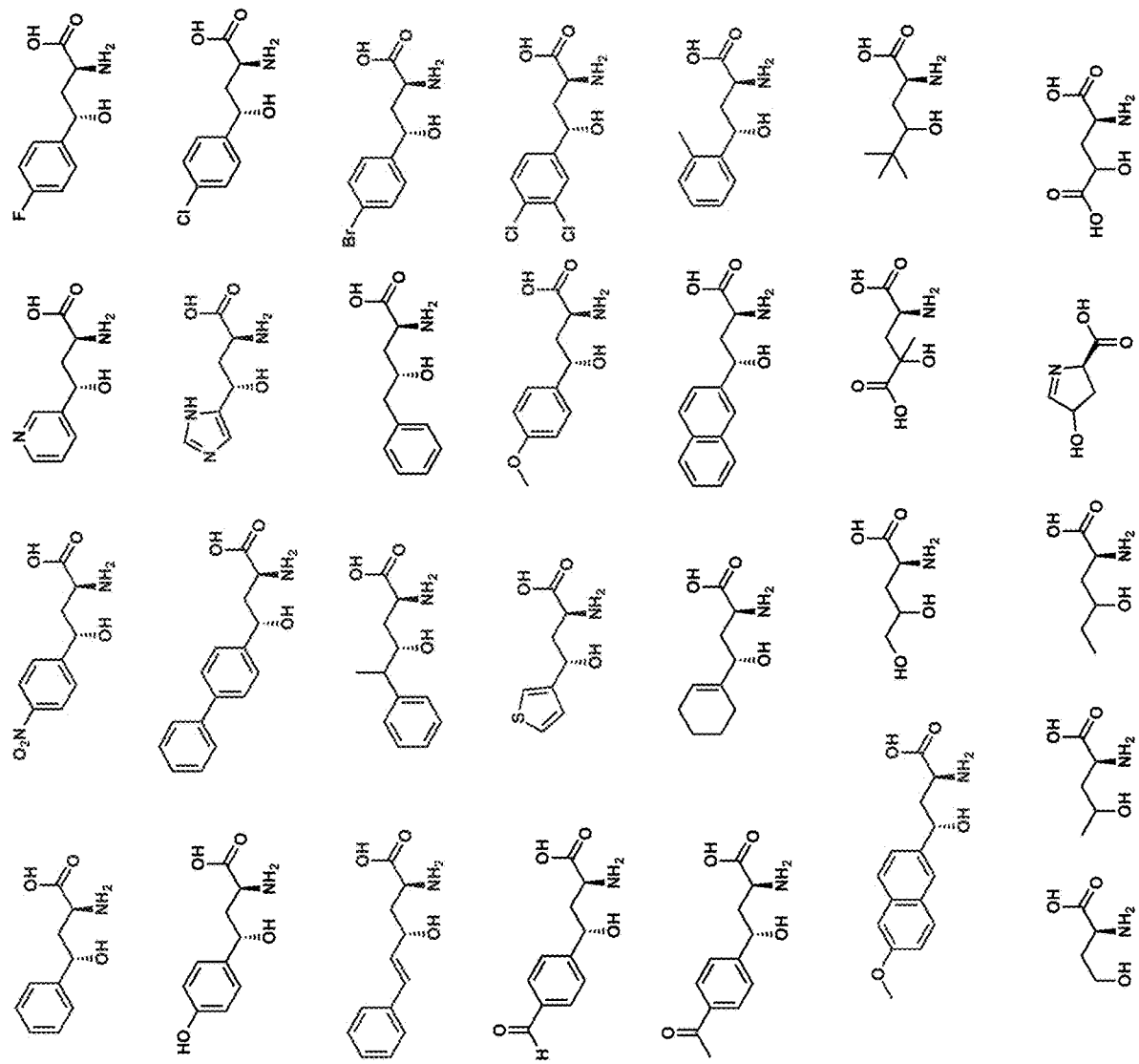

The inventors have found that UstD is able to catalyze the formation of a wide variety of γ-hydroxy amino acids, the vast majority of which show the formation of only a single diastereomer. See FIGS. 4 and 8. FIG. 4 shows non-limiting examples of suitable substrates for UstD. The wild-type enzyme was used for reactions shown in FIG. 4 and TTN values were calculated based on apparent conversion method, except for glycolaldehyde and pyruvate where comparison of reactions at two separate catalyst loadings followed by estimation was used. FIG. 8 shows a sampling of various gamma-hydroxy amino acid products that have been made using the method disclosed herein. These range from sterically demanding aryl aldehydes (biphenyl-4-carboxaldehyde) to electronically deactivated aryl aldehydes (4-hydroxybenzaldehyde) to aliphatic aldehydes (glycolaldehyde.) See FIGS. 5A and 5B. FIG. 5A depicts TTNs for the reaction using UstD$^{WT}$, UstD$^{ILM}$, UstD$^{FVF}$, and UstD$^{TLM}$ enzymes and the substrates/reactants biphenyl-4-carboxaldehyde, 4-methoxybenzaldehyde, and 2-methylbenzaldehyde. FIG. 5B shows corresponding results using glycoaldehyde as the substrate/reactant.

A reaction with 4-bromobenzaldehyde was done at preparative scale to produce ~50 mg of product:

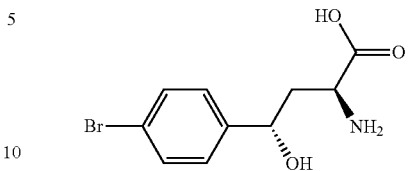

Figure 9:
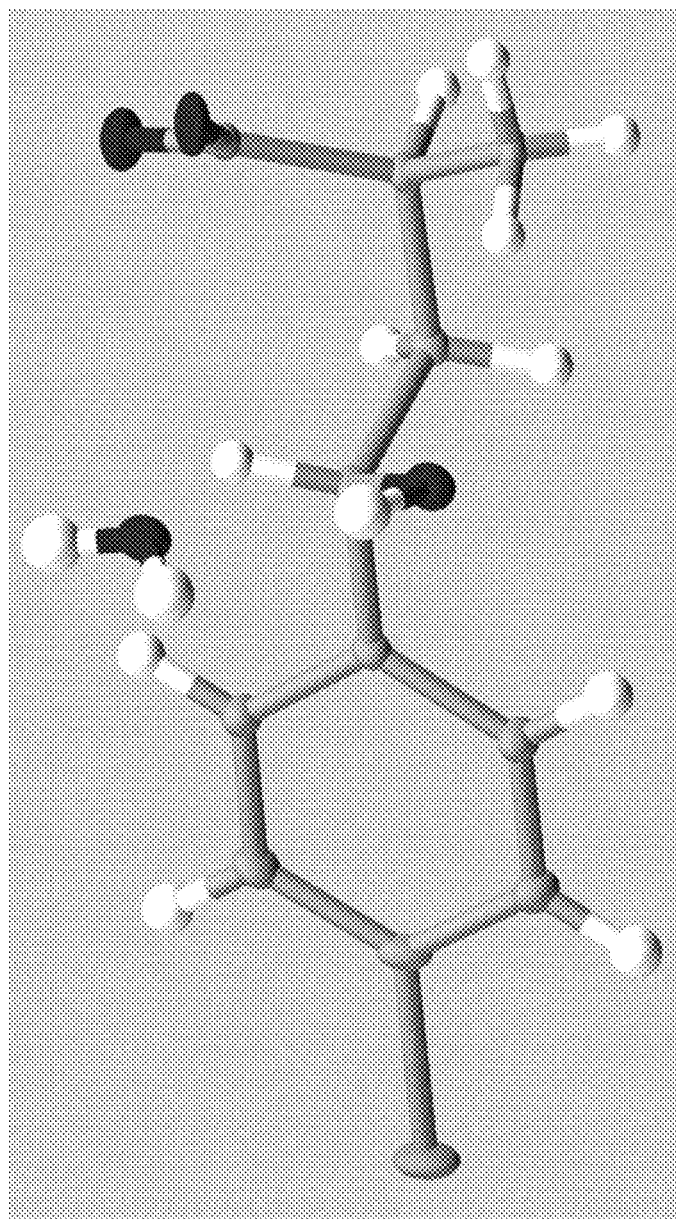
Figure 10:
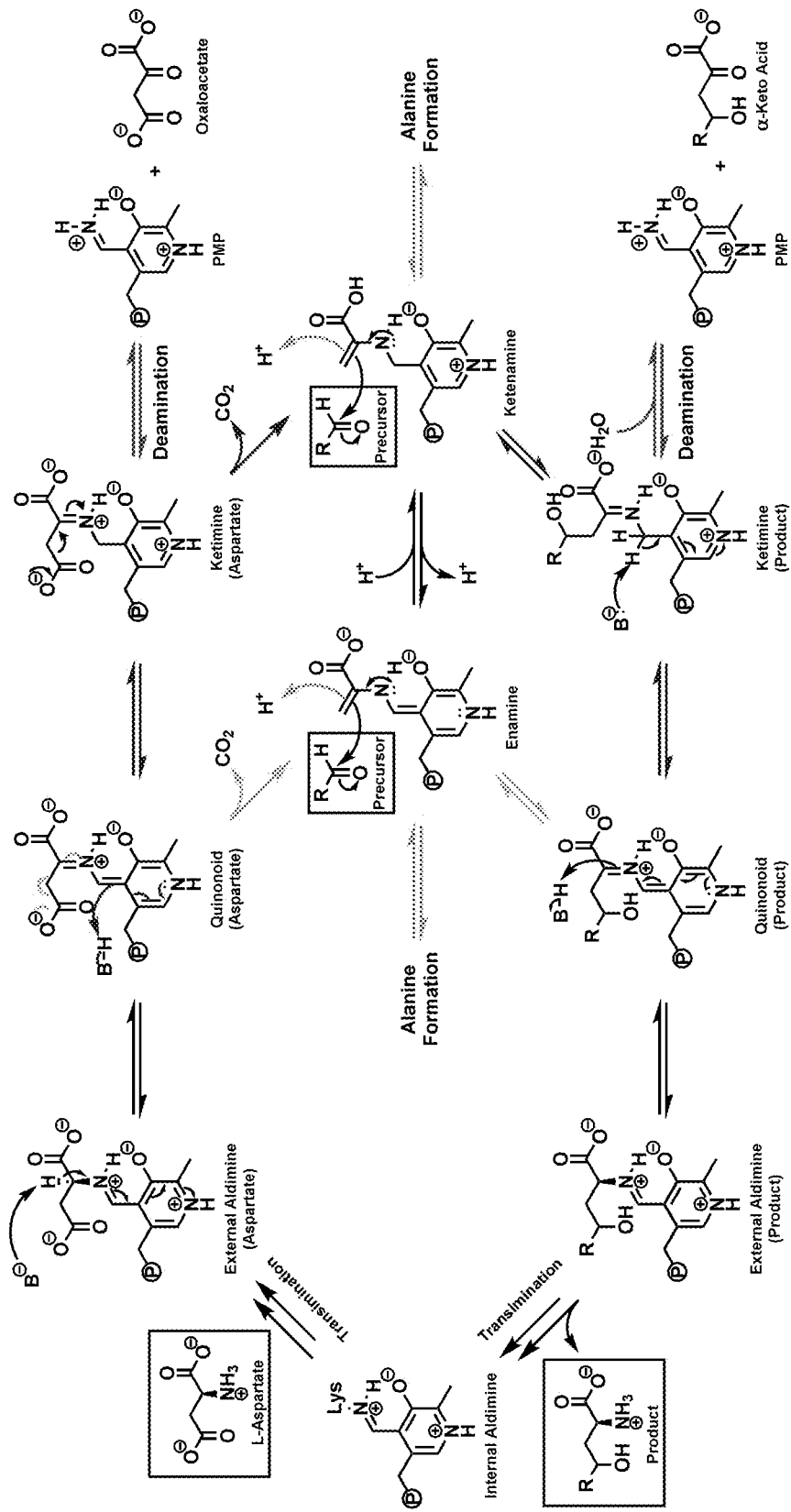
Figure 11A:
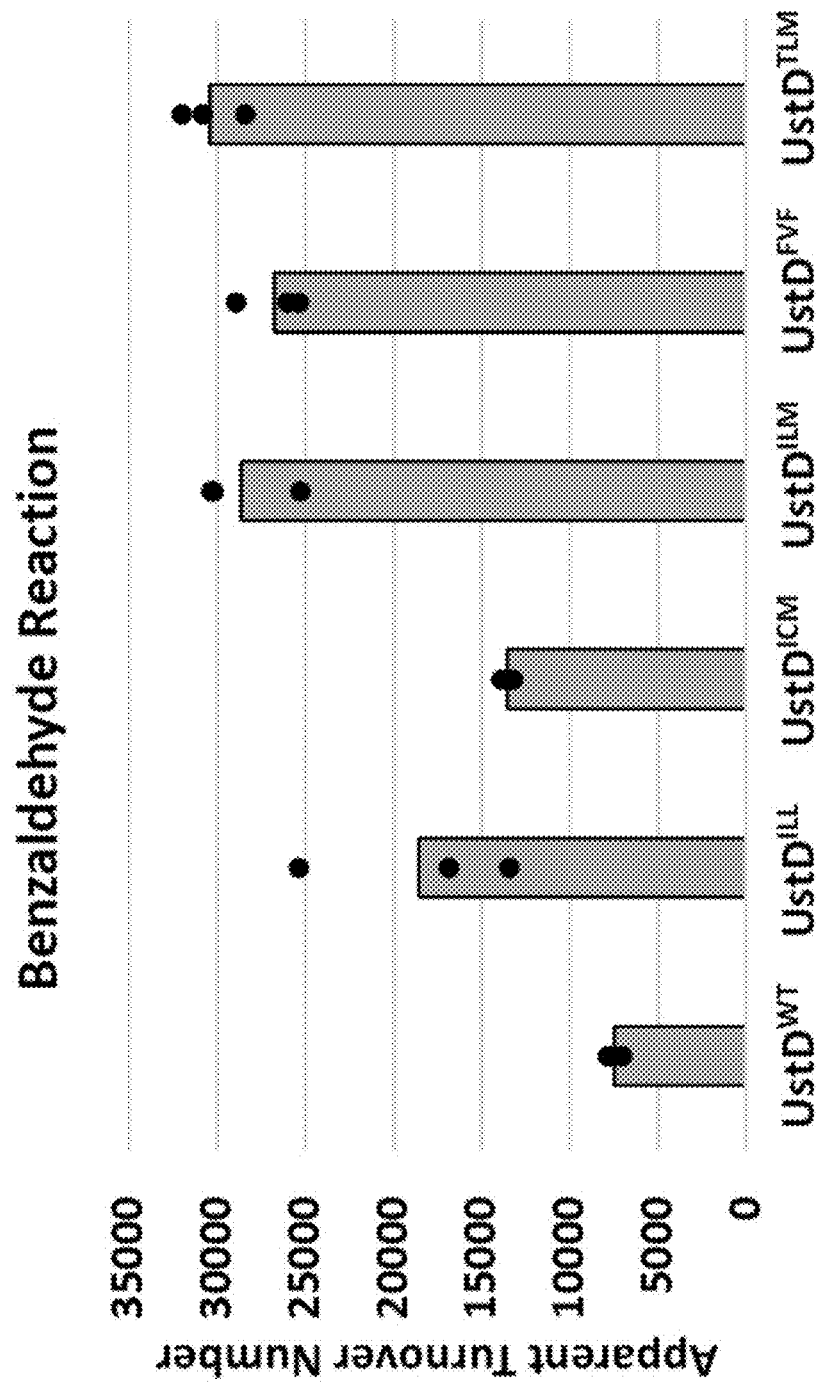
Figure 11B:
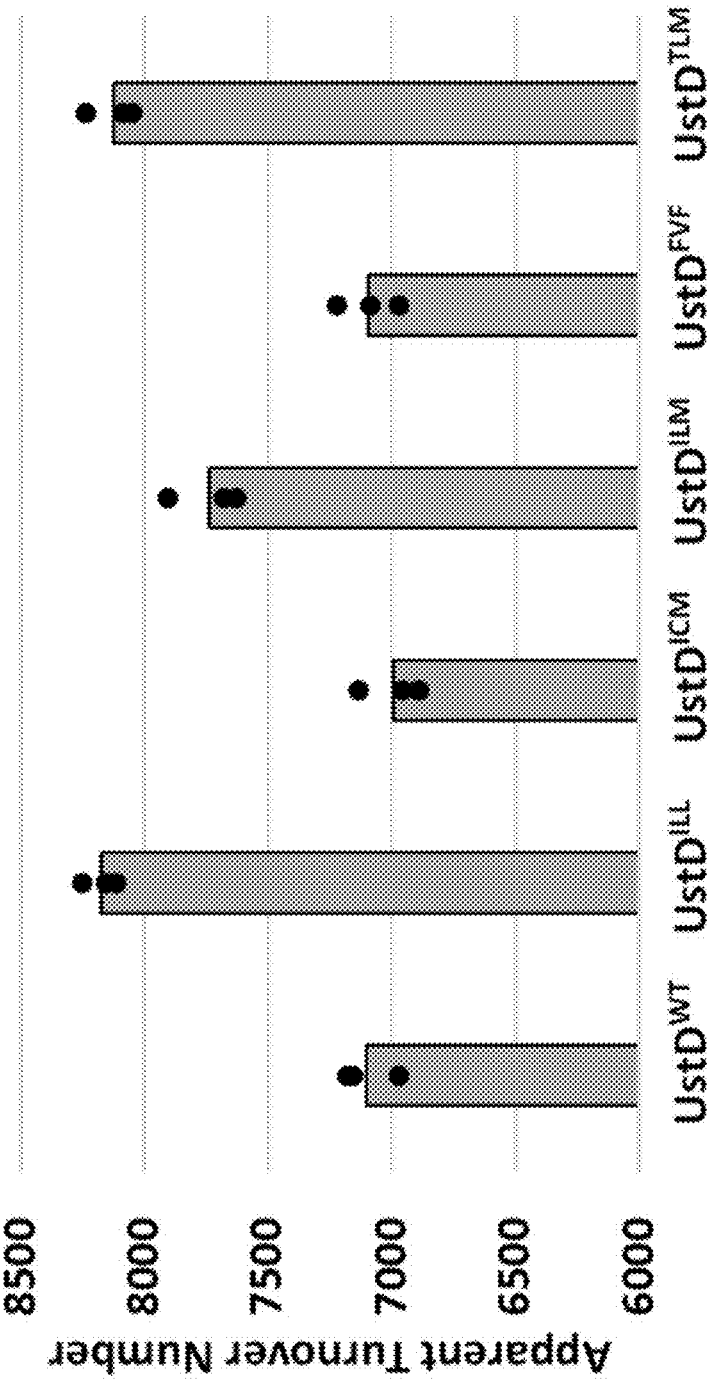
Figure 11C:
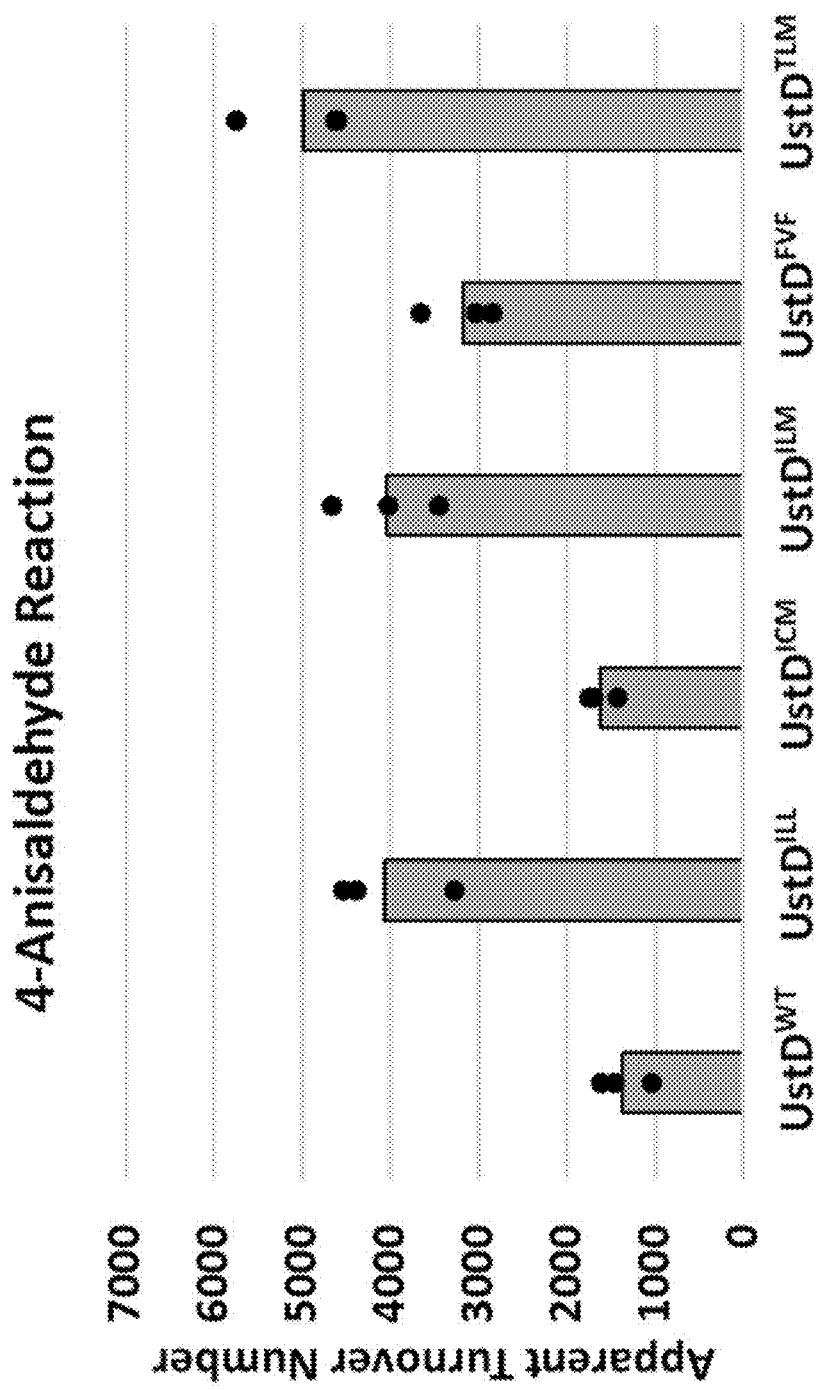
Figure 11D:
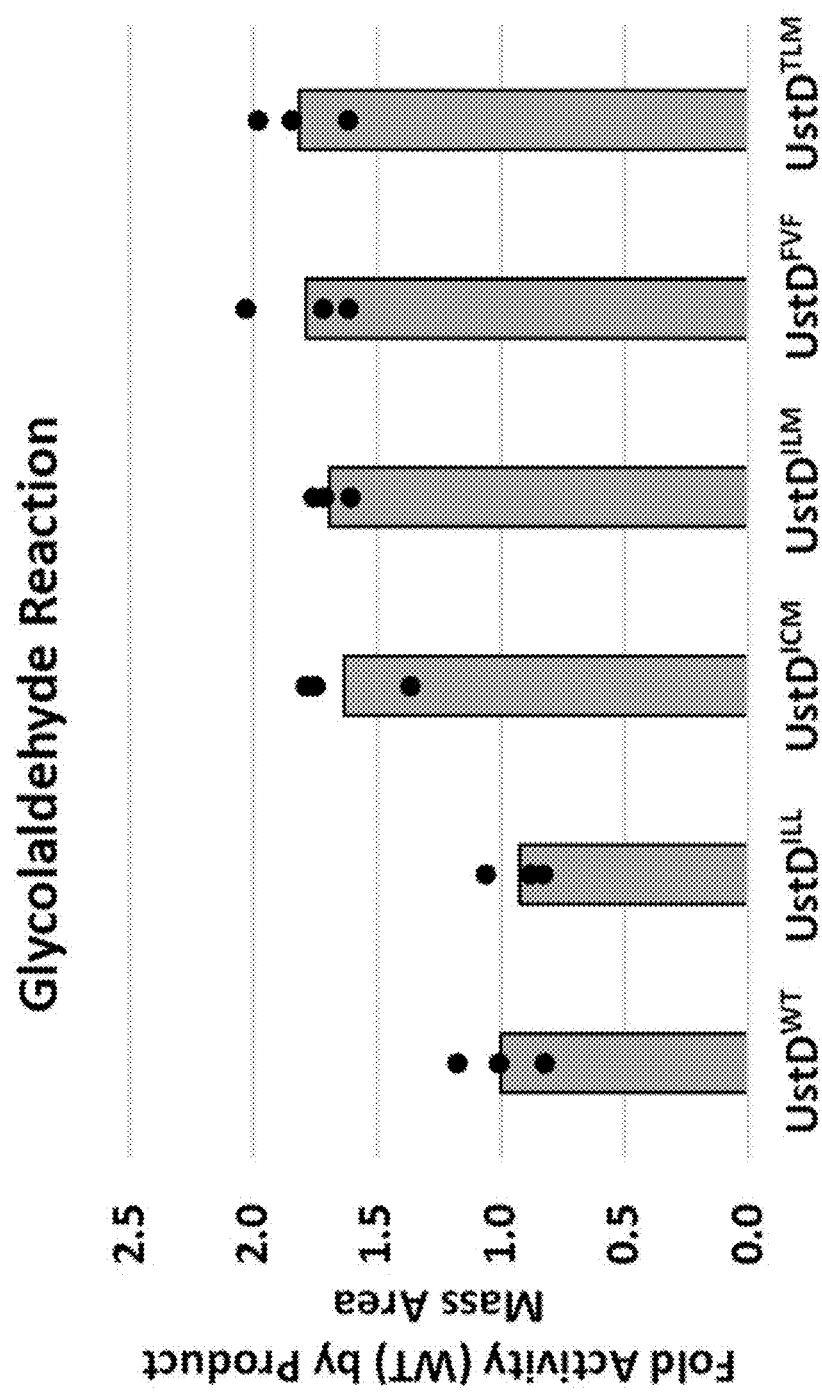

The corresponding amino acid product was crystallized, and small molecule crystallographic studies revealed the product retains the same absolute configuration as the native Ustiloxin B product. FIG. 9 depicts the 3D ball-and-stick model of the amino acid product. While a majority of the substrate scope exploration was done with the wild-type enzyme, early studies have shown that the increases in activity are general. Of note, both UstD$^{ILM}$ and UstD$^{TLM}$ have much higher TTNs for catalyzing a reaction with 4-methoxybenzaldehyde than does UstD$^{WT}$. Additionally, TTNs for reactions with biphenyl-4-carboxalehyde did not decrease, as one might have expected with a more sterically crowded catalyst such as UstD$^{FVF}$. These results show that UstD is engineerable as a generalized diastereoselective biocatalyst.

EXAMPLES

The following examples are included herein solely to provide a more complete description of the methods and materials disclosed herein. The examples are not intended to limit the scope of the claims in any way.

General Materials and Methods:

All chemicals and reagents were purchased from various international commercial suppliers at the highest quality available and used without further purification. These suppliers were Sigma-Aldrich Corporation (St. Louis, Mo., USA), VWR International, LLC (Radnor, Pa., USA), Chem-Impex International, Inc. (Wood Dale, Ill., USA), Alfa Aesar (Tewksbury, Mass., USA), and Combi-Blocks Inc. (San Diego, Calif., USA). E. coli cells were electroporated with an Eppendorf E-porator at 2500 V. New Brunswick I26R shaker incubators (Eppendorf) were used for cell growth. (Eppendorf North America, Hauppauge, N.Y., USA). Cell disruption via sonication was performed with a Sonic Dismembrator 550 sonicator (Thermo Fisher Scientific, Waltham, Mass., USA). Optical density and UV-vis spectroscopic measurements were collected on a UV-2600 Shimadzu spectrophotometer. (Shimadzu Corporation, Kyoto, Japan.) UPLC-MS data were collected on an Acquity®-brand UPLC equipped with an Acquity®-brand PDA and QDa®-brand MS detector using a using either a BEH C18 column for substituted benzaldehyde reactions (all from Waters Corporation, Millford, Mass., USA), or an Intrada Amino Acid column (Imtakt USA, Inc., Portland, Oreg., USA) for aliphatic aldehyde reactions. Preparative column separations were performed on an Isolera One Flash Purification system (Biotage, Uppsala, Sweden). NMR data were collected on Bruker 400 or 500 MHz spectrometers. (Bruker Corporation, Billerica, Mass., USA.) High-resolution mass spectrometry data were collected with a Q Extractive Plus Orbitrap instrument (NIH IS10OD020022-1) (ThermoFisher Scientific) with samples ionized by ESI.

Cloning of Wild-Type UstD:

A codon-optimized copy of the *Aspergillus flavus* UstD gene was purchased as a "gBlock"-brand, double-stranded DNA from Integrated DNA Technologies, Coralville, Iowa, USA (hereinafter "IDT"). This DNA fragment was inserted into a pET-22b(+) vector by the Gibson Assembly® method (Codex DNA, Inc., San Diego, Calif.) and transformed into electrocompetent BL21(DE3) *E. coli* cells via electroporation. (Gibson, D. G. et al. Enzymatic assembly of DNA molecules up to several hundred kilobases. *Nat. Methods* 6, 343-345 (2009).) After a 30-minute recovery period in Luria-Burtani (LB) media, cells were plated onto LB plates containing 100m/mL ampicillin ($LB_{amp}$) and incubated overnight. A single colony was then used to inoculate 50 mL of Terrific Broth II media containing 100 µg/mL ampicillin ($TB_{amp}$), which was then incubated overnight at 37° C. with shaking at 200 rpm. 500 µL of the saturated cell culture was then mixed with 500 µL of sterile 80% glycerol and snap-frozen in liquid nitrogen to generate a glycerol stock.

Protein and DNA Sequences:

The protein sequence of UstD (Uniprot accession code: XP_002381324.1) is:

```
                                                (SEQ. ID. NO: 1)
MKSVATSSLD  DVDKDSVPLG  SSINGTAQAE  TPLENVIDVE

SVRSHFPVLG  GETAAFNNAS  GTVVLKEAIE  STSNFMYSFP

FPPGVDAKSM  EAITAYTGNK  GKVAAFINAL  PDEITFGQST

TCLFRLLGLS  LKPMLNNDCE  IVCSTLCHEA  AASAWIHLSR

ELGITIKWWS  PTTTPNSPDD  PVLTTDSLKP  LLSPKTRLVT

CNHVSNVVGT  IHPIREIADV  VHTIPGCMLI  VDGVACVPHR

PVDVKELDVD  FYCFSWYKLF  GPHLGTLYAS  RKAQDRYMTS

INHYFVSSSS  LDGKLALGMP  SFELQLMCSP  IVSYLQDTVG

WDRIVRQETV  LVTILLEYLL  SKPSVYRVFG  RRNSDPSQRV

AIVTFEVVGR  SSGDVAMRVN  TRNRFRITSG  ICLAPRPTWD

VLKPKSSDGL  VRVSFVHYNT  VEEVRAFCSE  LDEIVTRDT
```

The DNA sequence of UstD (codon optimized using IDT Codon Optimization Tool (IDT), bearing a flanking Gibson Assembly® insertion site (Codex DNA, Inc., San Diego, Calif.) and C-terminal 6×His-Tag sequences is:

```
                                        (SEQ. ID. NO: 2)
GTTTAACTTTAAGAAGGAGATATACATATGAAGAGCGTAGCGACG

AGTTCCCTTGATGACGTAGATAAAGATTCCGTCCCCCTGGGCAGT

TCGATCAATGGCACTGCACAAGCGGAAATCCGCTGGAGAATGTGA

TCGACGTCGAATCAGTGCGCTCACATTTCCCGGTATTAGGGGGGG

AAACGGCCGCGTTTAACAATGCATCAGGAACCGTAGTTTTGAAGG

AGGCAATTGAATCGACTTCAAATTTCATGTATAGCTTTCCTTTTC

CCCCGGGTGTTGACGCTAAGTCAATGGAGGCTATTACCGCATATA

CGGGGAATAAGGGCAAGGTTGCGGCATTTATCAATGCACTTCCTG

ATGAAATTACATTCGGGCAGTCCACAACTTGTCTGTTCCGTTTAT

TAGGTCTGTCGCTTAAACCTATGCTGAATAACGATTGTGAAATCG

TATGCTCAACATTATGTCACGAAGCAGCAGCTTCCGCATGGATTC

ATTTAAGTCGCGAATTAGGAATTACCATTAAGTGGTGGAGCCCAA

CTACTACACCGAATAGTCCCGATGATCCAGTTCTGACGACTGACT

CATTGAAGCCCTTGCTTAGTCCAAAAACGCGCCTTGTTACATGTA

ATCACGTGTCGAATGTTGTAGGAACCATCCACCCTATTCGTGAGA

TTGCCGACGTGGTACATACCATTCCTGGATGCATGCTTATCGTTG

ACGGTGTGGCATGTGTCCCGCATCGTCCAGTTGATGTTAAAGAAT

TGGATGTAGATTTTTACTGCTTTTCCTGGTACAAGTTGTTCGGAC

CGCATCTTGGAACCCTGTATGCTTCCCGCAAAGCCCAAGACCGCT

ATATGACCTCAATTAACCATTACTTCGTCTCATCGTCGAGCCTTG

ATGGTAAGCTGGCATTAGGCATGCCGTCCTTTGAACTGCAGTTGA

TGTGCTCTCCAATTGTTTCGTATTTGCAAGATACGGTGGGCTGGG

ACCGTATCGTGCGCCAAGAGACTGTGCTGGTAACTATTTTGTTGG

AGTATTTACTTAGCAAGCCATCTGTATATCGTGTGTTCGGACGTC

GTAATTCTGATCCCAGTCAGCGTGTAGCAATCGTAACTTTTGAAG

TCGTGGGACGTAGTTCCGGGGATGTGGCAATGCGCGTAAATACGC

GTAATCGCTTCCGCATTACCTCTGGAATTTGCCTGGCACCGCGCC

CGACATGGGACGTCTTGAAACCGAAGAGTAGCGACGGACTTGTTC

GCGTCAGCTTTGTACATTACAACACGGTTGAGGAAGTGCGTGCGT

TCTGCAGCGAGTTAGACGAGATTGTGACACGCGACACCCTCGAGC

ACCATCACCATCACCATTGAGATCCGGCTGC
(Bold underlined residues show the start codon
and the 6X His tag. The encoded protein is
shown in SEQ. ID. NO: 3.)
```

Production of UstD Degenerate Codon Libraries:

Saturation mutagenesis libraries were generated using the 22-codon trick. (Kille et al. Reducing Codon Redundancy and Screening Effort of Combinatorial Protein Libraries Created by Saturation Mutagenesis, *ACS Synth. Biol.* 2013, 2, 2, 83-92 (Jun. 15, 2012).) Reactions were assembled by adding the following to a PCR tube: 32 µL H2O, 10 µL 5× Phusion®-brand GC buffer (NEB), 1 µL 10 mM dNTP mix, 1 µL 10 µM forward primer mix, 1 µL 10 µM reverse primer, 1 µL~100 ng/µL parent plasmid, 0.5 µL Phusion®-brand polymerase (NEB). Reaction annealing temperatures were varied between libraries to optimize amplification.

Production of UstD Random Mutagenesis Libraries:

Random mutagenesis was carried out via error-prone PCR. Reaction conditions were optimized to generate 1-2 codon mutations per plasmid. Reactions were assembled by adding the following to a PCR tube: 32 µL H2O, 5 µL 10× Taq buffer (NEB), 1 µL 10 mM dNTP mix, 1 µL 10 µM internal forward primer, 1 µL 10 µM internal reverse primer, 1 µL~100 ng/µL parent plasmid, 6.5 µL 50 mM $MgCl_2$, 2.5 µL 1 mM $MnCl_2$, 1 µL DMSO, 0.5 µL Taq polymerase (NEB). Reactions were carried out in a thermocycle at 55° C. for an annealing temperature.

Linear Regression Model Guided Cysteine Shuffle Library Production

Sequence alignment and homology modeling were used to target five cysteines which were predicted to be on the surface of UstD and were predicted to be amiable to mutagenesis. A degenerate codon library of the following design was created using polymerase cycling assembly:

| Position | Degenerate Codon | Possible Amino Acids |
|---|---|---|
| C122 | KBC | A, C, G, F, S, V |
| C139 | TSC | C, S |
| C227 | KSC | A, C, G, S |
| C236 | TSK | C, S, W |
| C428 | KSC | A, C, G, S |

See SEQ. ID. NO: 14.

Transformation and screening were conducted for two plates (180 maximum possible variants) as described above, where three control wells were present for UstD$^{TLM}$ and UstD$^{WT}$ each and UstD$^{TLM}$ was treated as the parent enzyme for the plate for relative fold activity calculation. One glycerol stock plate of each screened plate was sent for sequencing (Functional Biosciences, Madison, Wis., USA), and the resulting sequencing data were analyzed using SnapGene®-brand software (GSL Biotech LLC, Chicago, Ill. USA) for sequencing integrity and complete sequencing of all variant positions for each well. Of the 192 wells (including controls), 111 successful reads were obtained with 98 unique sequences. Sequences were stored by concatenating the identity of each position mutated in the library, such that the parent sequence is represented as "CCCCC". That is, the wt protein has a cysteine residue at all of positions 122, 139, 227, 236, and 428. Any mutation at any of those five positions is indicated by the appropriate one-letter amino acid code. The resulting sequences were paired with their corresponding relative fold-activity values in a .csv file. All data analysis at this stage was conducted using Python®-brand software (Python Software Foundation, Beaverton, Oreg., USA) version 3.6.8 with the Scikit-Learn® 0.20.3 package (Institute National de Recherche en Informatique et en Automatique, Le Chesnay, France and Telecom Paris Tech, Paris, France). The analysis workflow was conducted as follows:

1. Filter all sequence-activity pairings which have an activity less that 0.1 (79 pairings removed, 32 remained)
2. Take the negative log of all activity values
3. One-hot encode all remaining sequences
4. Perform leave-one-out cross-validation (LOOCV) linear regression modelling to ensure model integrity
5. Fit linear regression model to all data
6. Construct all possible sequences reachable from the filtered sequence space, and one-hot encode each
7. Generate activity predictions for all possible sequences within the sequence space
8. Take the exponential of all negative activities
9. Sort by predicted relative fold-activity From this dataset, two sequences bearing three mutated cysteines (UstD$^{TLM-ACASC}$ and UstD$^{TLM-ASCSC}$) and one sequence bearing four mutated cysteines (UstD$^{TLM-ASASC}$) were chosen for cloning and expression.

These genes were generated from a lower activity sequence found during screening (UstD$^{TLM-ASACC}$) using PCA, and were tested in both whole cell catalyst and purified catalyst analytical scale reactions against UstD$^{TLM}$ and the top hit from the screened plates (UstD$^{TLM-SCASC}$). Protein expression yields were determined by standard Bradford assay techniques.

| Variant | mg Protein/L Culture | Purified Protein Fold-Activity | Whole Cell Fold-Activity |
|---|---|---|---|
| UstD$^{TLM}$ | 8 | 1.0 | 1.0 |
| UstD$^{TLM-SCASC}$ | 48 | 0.7 | 1.4 |
| UstD$^{TLM-ASASC}$ | 33 | 0.6 | 1.3 |
| UstD$^{TLM-ACASC}$ | 48 | 0.7 | 2.4 |
| UstD$^{TLM-ASCSC}$ | 40 | 0.7 | 1.6 |

For clarity, these unnatural, isolated, mutated proteins contain the following mutations relative to the wild-type:

UstD$^{TLM-ACASC}$: I391T-C392L-L393M-C122A-C227A-C236S (SEQ. ID. NO: 9)

UstD$^{TLM-ACASC}$: I391T-C392L-L393M-C122A-C1395-C236S (SEQ. ID. NO: 10)

UstD$^{TLM-ACASC}$: I391T-C392L-L393M-C122A-C1395-C227A-C236S (SEQ. ID. NO: 11)

UstD$^{TLM-ACASC}$: I391T-C392L-L393M-C122A-C1395-C227A (SEQ. ID. NO: 12)

UstD$^{TLM-ACASC}$: I391T-C392L-L393M-C1225-C227A-C236S (SEQ. ID. NO: 13)

UstD Variant Library Screening:

Library DNA pools were transformed into electrocompetent E. coli BL21(DE3) cells using standard electroporation techniques. The resulting transformed mixture was then plated on LB agar plates containing 100m/mL ampicillin and allowed to grow for 16 h. Starter culture plates were made by adding 600 µL of TB$_{amp}$ to each well of sterile 96-deep-well plates (2 mL well volume). Column 6 of each plate was used as a control column, where three wells were inoculated with individual colonies of E. coli harboring a pET-22b(+) plasmid encoding the parent variant of the library. An additional three wells were inoculated with E. coli harboring pET-22b(+) plasmids encoding a random enzyme of distinct function from UstD. The final two wells, typically at the center of the plate, were left uninoculated and serve as sterile controls to confirm there was no general contamination of the plate or well-to-well contamination. The plates were then covered with a loose plastic 96-well plate cover. The plates were then incubated overnight in a 37° C. shaker incubator at 200 rpm. Glycerol stock plates were made in duplicate for each overnight culture plate by adding 100 µL of each well to a 350 µL plate, followed by 100 µL of sterile 50% glycerol with mixing by repeated pipetting. Glycerol stock plates were stored at −80° C. Expression plates were made by adding 600 µL of TB$_{amp}$ to each well of sterile 96-deep-well plates, and 5 µL of the overnight starter plates were transferred to matching wells in the expression plates. These plates incubated for 2 h at 37° C. in a shaker incubator at 200 rpm. The plates were then transferred to an ice bed and incubated for an additional 30 min. Protein expression was induced by adding 33 µL of 1 mM IPTG dissolved in TB$_{amp}$ to each well, and the plates were transferred to a 20° C. shaker incubator at 200 rpm and incubated for 16 h. The plates were then spun down at 5000×g for 30 min to pellet cells, and the supernatant was discarded. The cells were then resuspended in 400 µL of lysis buffer containing: 100 mM potassium phosphate buffer pH 7.0, 100 mM sodium chloride, 500 µM PLP, 2 mM MgCl$_2$, 1 mg/mL lysozyme, and 0.01 mg/mL DNase. Lysis was conducted in a 37° C. incubator for 1 h before the plates were spun down at 5000×g for 30 min. Reaction plates were created by transferring a small amount (150-300 µL, depending on expected activity per well) to sterile 96-deep-well plates, and a reaction master mix was added to each well so that the final concentration of reaction components was: 5% DMSO, 25 mM L-aspartate, 25 mM benzaldehyde. The plates were then sealed with a rubber gasket to prevent evaporation, and the plates were incubated at 37° C. for 16 h. An equal volume to the end well volumes of acetonitrile was added to each well of the reaction plates, and the plates were gently vortexed to facilitate mixing. The plates were then spun down at 5000×g, and 250 µL of supernatant from each well was transferred to a 96-well filter plate placed on top of a 96-well LC-MS sample plate. The plates were spun at 1000×g to filter the supernatants of any large particles, and the LC-MS plates were sealed with a plastic cover. The plates were then analyzed by UPLC-MS as per analytical scale reactions. Relative fold-activity quantification was calculated by dividing the observed product 210 nm peak area or 197.00 m/z MS-SIR peak area by the average parent control well area for the same plate.

Expression and Purification of UstD:

An overnight culture was created by inoculating 50 mL of $TB_{amp}$ media with a single colony of freshly transformed *E. coli* BL21(DE3) harboring a pET-22b(+) plasmid encoding the enzyme variant, as described above. This culture was shaken at 37° C. and 200 rpm for roughly 16 h. 10 mL of overnight culture was then used to inoculate 1 L of $TB_{amp}$, which was shaken at 37° C. and 200 rpm for approximately 1.5 h or until an optical density (600 nm) of 0.4-0.6 was reached. Cultures were cooled on ice for 30 min and then induced by adding IPTG to a final concentration of 50 µM. The cultures were allowed to continue to grow for an additional 16 h at 20° C. and shaking at 200 rpm. Cells were then harvested by centrifugation (4° C., 30 min, 4,000×g), and the cell pellets were stored at −20° C. overnight.

To purify UstD, cell pellets were thawed on ice and then resuspended in lysis buffer (50 mM potassium phosphate buffer (pH 8.0)+100 mM sodium chloride (enzyme storage buffer), 20 mM imidazole, 1 mg/mL Hen Egg White Lysozyme (Gold Biotechnology, Inc., St. Louis, Mo., USA, hereinafter "GoldBio"), 0.2 mg/mL DNaseI (GoldBio), 1 mM $MgCl_2$, 150 µM pyridoxal 5'-phosphate (PLP)). A volume of 4 mL of lysis buffer was used per gram of wet cell pellet. After 1 h of stirring at 37° C., the resuspended cells were lysed using sonication (20 min, 0.8 seconds on, 0.2 seconds off, power setting 5). The resulting lysate was then spun down at 75,600×g to pellet cellular debris. Ni/NTA beads (pre-equilibrated in 50 mM potassium phosphate buffer (pH 8.0), 100 mM sodium chloride, 20 mM imidazole) were added to the supernatant and incubated on ice for 1 h. The beads were then collected in a column, and the flow-through was recycled once to wash any remaining beads from the original vessel. The column was washed with 10 column volumes of enzyme storage buffer containing 20 mM imidazole, followed by sequential 10 column volume washes of enzyme storage buffer containing 40 mM and 60 mM imidazole. Elution was done by adding storage buffer containing 250 mM imidazole and collecting the flow-through until the eluent was no longer yellow (color due to the enzymatically bound PLP cofactor). The eluent was then transferred to a centrifugal filter tube (Amicon®-brand Ultra-15, 30 kDa MWCO, Millipore-Sigma, Burlington, Mass., USA) and concentrated by centrifugation (4,000×g, 15 min). Imidazole was then removed through repeated dilution (with enzyme storage buffer) and concentration steps until no more than 100 nM imidazole was present. The buffer exchanged enzyme was then flash frozen as small droplets by dripping the solution into liquid nitrogen, transferred to a conical vial, and stored at −80° C. for no more than 1 month before use.

UstD for enzymatic reactions was obtained by thawing an appropriate quantity of stored frozen droplets on ice. Thawed protein was then centrifuged at 20,000×g to remove any aggregated protein. Protein concentration was determined by Bradford assay.

Whole Cell Biocatalyst Reactions:

Cells harboring expressed UstD were made using the standard expression protocol described previously. Harvested cells were resuspended in 100 mM potassium phosphate buffer+100 mM sodium chloride pH 7.0 to a concentration of 100 mg/mL cells and stored at −20° C. until needed. Analytical scale reactions were carried out as described previously, replacing the added purified UstD and PLP with an appropriate amount of whole cell catalyst solution (typically to an end concentration of ~10 mg/mL cells) that was thawed on ice.

Optimization of Reaction Conditions for UstD:

All optimization reactions were conducted at an analytical scale (100 µL). PLP and L-aspartate stock solutions were made with 100 mM potassium phosphate buffer containing 100 mM sodium chloride (reaction buffer) at the indicated pH. Post-reaction quenching was done by adding 100 µL of acetonitrile containing 1 mM tryptamine as an internal standard. Quenched reactions were then centrifuged at 20,000×g to remove aggregated protein, and diluted with 200 µL of 1:1 water:acetonitrile. Quantification of product formation was performed by UPLC analysis, using integrated UV-vis peak areas at 210 nm. Variability in injection volumes were corrected by dividing peak areas by the observed internal standard peak area. Optimization for each component are listed below.

1) PLP Concentration

A 0.5 dram (3.7 mL) glass vial was charged with 82.7 µL reaction buffer (pH 8.0), 5 µL 500 mM benzaldehyde (2.5 µmol, 1 equiv, 25 mM final concentration) in DMSO (5% final concentration), 5 µL 500 mM L-aspartate (2.5 µmol, 1 equiv, 25 mM final concentration), and 2.3 µL of variable concentration PLP solutions (0-50 equivalents relative to final enzyme concentration). Reactions were initiated by adding 2.3 µL of 148 µM UstD (0.013% mol cat., 7500 max TON). Reactions vials were placed in a dark 37° C. incubator for 16 h.

2) L-Aspartate Concentration

A 0.5 dram (3.7 mL) glass vial was charged with 34.4 µL reaction buffer (pH 8.0), 5 µL 500 mM benzaldehyde (2.5 µmol, 1 equiv, 25 mM final concentration) in DMSO (5% final concentration), 8.3 µL 1 mM PLP (50 equivalents relative to final enzyme concentration), and 50 µL of variable concentration L-aspartate solutions (2.5-25 µmol, 1-10 equiv, 25-250 mM final concentration). Reactions were initiated by adding 2.2 µL of 75 µM UstD (0.007% mol cat., 15000 max TON). Reactions vials were placed in a dark 37° C. incubator for 16 h.

3) pH

A 0.5 dram (3.7 mL) glass vial was charged with 62.3 µL reaction buffer (variable pH), 5 µL 500 mM benzaldehyde (2.5 µmol, 1 equiv, 25 mM final concentration) in DMSO (5% final concentration), 25 µL 500 mM L-aspartate (12.5 µmol, 5 equiv, 125 mM final concentration), and 5 µL 1 mM PLP (50 equivalents relative to final enzyme concentration). Reactions were initiated by adding 2.7 µL of 37 µM UstD (0.004% mol cat., 25000 max TON). Reactions vials were placed in a dark 37° C. incubator for 16 h.

Preparative Scale Production of Unprotected Gamma-Hydroxy Amino Acids:

Flash frozen UstD was thawed on ice and centrifuged at 15,000×g for 10 minutes to pellet any aggregated protein. A 50 mL round bottom flask was charged with a given aldehyde (0.1-0.5 mmol, 1.0 equiv, 25 mM final concentration), which was then dissolved in an appropriate amount of DMSO (5% v/v final concentration). This solution was then diluted with 100 mM potassium phosphate buffer (pH 7.0) containing 100 mM sodium chloride. L-Aspartic acid sodium salt monohydrate (0.5-2.5 mmol, 5.0 equiv, 125 mM final concentration) and 50 molar equivalents of pyridoxal-5'-phosphate (PLP) relative to final UstD concentration were then added, followed by addition of UstD (0.001-0.1% mol cat.) Reactions took place in the dark at 37° C. for 16 h. Product formation was assessed by UPLC-MS. After reaction completion, the reaction mixture was quenched with an equivalent volume of acetonitrile and centrifuged (4,000×g, 10 min) to remove aggregated UstD. The supernatant was then concentrated to ~2 mL by rotary evaporation and loaded onto a preparative reverse-phase C18 pre-equilibrated at 1:20 methanol:water. Purification was performed via gradient elution on an Isolera One Flash Purification system (Biotage). Fractions bearing product (confirmed by UPLC-MS sampling of fraction tubes) were pooled and evaporated to dryness by rotary evaporation. The product was then resuspended in a minimal quantity of water, transferred to a pre-weighed 20 mL scintillation vial, frozen, and subjected to lyophilization.

Preparative Scale Production of Fmoc-Protected Gamma-Hydroxy Amino Acids:

Reactions were carried out in an identical fashion to that of the unprotected amino acids up until the reaction quench. After reaction completion, the reaction mixture was titrated with 6 M sodium hydroxide to a pH of ~10. An appropriate quantity of Fmoc-Cl (0.6-3 mmol, 1.2 equiv of original reaction 1-aspartate) was then dissolved in an equivalent volume (relative to total reaction volume) of acetonitrile, which was then added to the alkaline reaction mixture. The reaction was then stirred at room temperature for 4 h. For aliphatic γ-hydroxy amino acid products, further work-up and purification was performed identical to that of the unprotected amino acids. For aromatic γ-hydroxy amino acids, the resulting reaction mixture was then subjected to rotary evaporation at 45° C. to 100 mbar to remove dissolved acetonitrile. The reaction was then titrated with 2 M citric acid until a pH of −3 to precipitate all Fmoc-protected amino acids (γ-hydroxy amino acid product, L-Aspartic Acid, L-Alanine.) The precipitated mixture was then extracted 3 times with 25 mL of ethyl acetate, and the aqueous phase was analyzed by UPLC-MS to ensure total product extraction. The isolated organic phase was then washed twice with a 25 mL saturated sodium chloride solution to help remove latent water and citric acid. This brine phase was also analyzed by UPLC-MS to ensure no product was lost during the washing phase. The organic phase was then dried over $MgSO_4$ and concentrated by rotary evaporation. The concentrated solution was tested by TLC against a variety of separating conditions (typically ethyl acetate:n-hexane at varying ratios) to determine ideal separating conditions. The concentrated solution was then loaded onto a Biotage Samplet unit and dried. A Biotage 25 g KP-Sil cartridge was pre-equilibrated to the initial separating conditions, and the Samplet bearing the crude product was inserted into the cartridge. Purification was facilitated by gradient elution and automated fraction collecton, and all fractions bearing compounds absorbing at 210 nm were tested by UPLC-MS to determine which fractions contained purified products. These fractions were then pooled and concentrated by rotary evaporation in a round-bottom until ~3 mL of liquid remained. The remaining liquid was then transferred to a pre-weighed 6 mL screw-cap vial, evaporated to dryness by rotary evaporation, and dried further overnight on a high vacuum system.

What is claimed is:

1. A method of making a gamma-hydroxy amino acid, the method comprising contacting an aldehyde-containing substrate, an amino acid, and an unnatural, mutated UstD (Ustiloxin B biosynthesis protein D) enzyme having at least 90% sequence identity but less than 100% sequence identity to a wild-type UstD enzyme as shown in SEQ ID NO: 1, under conditions and for a time sufficient to react at least a portion of the aldehyde-containing substrate with at least a portion of the amino acid, to yield a gamma-hydroxy amino acid product.

2. The method of claim 1, wherein the aldehyde-containing substrate is present at a concentration and the amino acid is present at a concentration at least 4-fold higher than the concentration of the aldehyde-containing substrate.

3. The method of claim 1, wherein the aldehyde-containing substrate is present at a concentration and the amino acid is present at a concentration at least 10-fold higher than the concentration of the aldehyde-containing substrate.

4. The method of claim 1, further comprising contacting the aldehyde-containing substrate, the amino acid, and the unnatural, mutated UstD enzyme in the presence of pyridoxal 5'-phosphate.

5. The method of claim 4, wherein the aldehyde-containing substrate is present at a concentration and the amino acid is present at a concentration at least 4-fold higher than the concentration of the aldehyde-containing substrate.

6. The method of claim 4, wherein the aldehyde-containing substrate is present at a concentration and the amino acid is present at a concentration at least 10-fold higher than the concentration of the aldehyde-containing substrate.

7. The method of claim 4, wherein the unnatural, mutated UstD enzyme is present at a concentration and the pyridoxal 5'-phosphate is present at a concentration at least 20-fold higher than the concentration of the unnatural, mutated UstD enzyme.

8. The method of claim 7, wherein the aldehyde-containing substrate is present at a concentration and the amino acid is present at a concentration at least 4-fold higher than the concentration of the aldehyde-containing substrate.

9. The method of claim 7, wherein the aldehyde-containing substrate is present at a concentration and the amino acid is present at a concentration at least 10-fold higher than the concentration of the aldehyde-containing substrate.

10. The method of claim 4, wherein the unnatural, mutated UstD enzyme is present at a concentration and the pyridoxal 5'-phosphate is present at a concentration at least 40-fold higher than the concentration of the unnatural, mutated UstD enzyme.

11. The method of claim 10, wherein the aldehyde-containing substrate is present at a concentration and the amino acid is present at a concentration at least 4-fold higher than the concentration of the aldehyde-containing substrate.

12. The method of claim 10, wherein the aldehyde-containing substrate is present at a concentration and the amino acid is present at a concentration at least 10-fold higher than the concentration of the aldehyde-containing substrate.

13. The method of claim 1, wherein the unnatural, mutated UstD enzyme comprises an amino acid sequence as shown in SEQ ID NO: 1, wherein at least one residue selected from positions 122, 139, 227, 236, and 428, is not cysteine.

14. The method of claim 1, wherein the unnatural, mutated UstD enzyme comprises an amino acid sequence selected from the group consisting of SEQ ID NOs: 4, 5, 6, 7, 8, 9, 10, 11, 12, and 13.

* * * * *

SEQUENCE LISTING

```
<160> NUMBER OF SEQ ID NOS: 14

<210> SEQ ID NO 1
<211> LENGTH: 439
<212> TYPE: PRT
<213> ORGANISM: Aspergillus flavus

<400> SEQUENCE: 1

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
        115                 120                 125
```

```
Leu Ser Leu Lys Pro Met Leu Asn Asn Asp Cys Glu Ile Val Cys Ser
    130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Thr Pro Asn
                    165                 170                 175

Ser Pro Asp Asp Pro Val Leu Thr Thr Asp Ser Leu Lys Pro Leu Leu
                180                 185                 190

Ser Pro Lys Thr Arg Leu Val Thr Cys Asn His Val Ser Asn Val Val
            195                 200                 205

Gly Thr Ile His Pro Ile Arg Glu Ile Ala Asp Val Val His Thr Ile
    210                 215                 220

Pro Gly Cys Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
                260                 265                 270

Ala Gln Asp Arg Tyr Met Thr Ser Ile Asn His Tyr Phe Val Ser Ser
            275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
                340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
    370                 375                 380

Phe Arg Ile Thr Ser Gly Ile Cys Leu Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
                420                 425                 430

Glu Ile Val Thr Arg Asp Thr
    435

<210> SEQ ID NO 2
<211> LENGTH: 1382
<212> TYPE: DNA
<213> ORGANISM: Aspergillus flavus
<220> FEATURE:
<221> NAME/KEY: CDS
<222> LOCATION: (28)..(1368)

<400> SEQUENCE: 2
gtttaacttt aagaaggaga tatacat atg aag agc gta gcg acg agt tcc ctt    54
                             Met Lys Ser Val Ala Thr Ser Ser Leu
                               1               5 gat gac gta gat aaa gat tcc gtc ccc ctg ggc agt tcg atc aat ggc    102
Asp Asp Val Asp Lys Asp Ser Val Pro Leu Gly Ser Ser Ile Asn Gly
 10              15                  20                  25
```

```
act gca caa gcg gaa act ccg ctg gag aat gtg atc gac gtc gaa tca      150
Thr Ala Gln Ala Glu Thr Pro Leu Glu Asn Val Ile Asp Val Glu Ser
            30                  35                  40 gtg cgc tca cat ttc ccg gta tta ggg ggg gaa acg gcc gcg ttt aac      198
Val Arg Ser His Phe Pro Val Leu Gly Gly Glu Thr Ala Ala Phe Asn
                45                  50                  55 aat gca tca gga acc gta gtt ttg aag gag gca att gaa tcg act tca      246
Asn Ala Ser Gly Thr Val Val Leu Lys Glu Ala Ile Glu Ser Thr Ser
        60                  65                  70 aat ttc atg tat agc ttt cct ttt ccc ccg ggt gtt gac gct aag tca      294
Asn Phe Met Tyr Ser Phe Pro Phe Pro Pro Gly Val Asp Ala Lys Ser
    75                  80                  85 atg gag gct att acc gca tat acg ggg aat aag ggc aag gtt gcg gca      342
Met Glu Ala Ile Thr Ala Tyr Thr Gly Asn Lys Gly Lys Val Ala Ala
90                  95                  100                 105 ttt atc aat gca ctt cct gat gaa att aca ttc ggg cag tcc aca act      390
Phe Ile Asn Ala Leu Pro Asp Glu Ile Thr Phe Gly Gln Ser Thr Thr
                110                 115                 120 tgt ctg ttc cgt tta tta ggt ctg tcg ctt aaa cct atg ctg aat aac      438
Cys Leu Phe Arg Leu Leu Gly Leu Ser Leu Lys Pro Met Leu Asn Asn
            125                 130                 135 gat tgt gaa atc gta tgc tca aca tta tgt cac gaa gca gca gct tcc      486
Asp Cys Glu Ile Val Cys Ser Thr Leu Cys His Glu Ala Ala Ala Ser
        140                 145                 150 gca tgg att cat tta agt cgc gaa tta gga att acc att aag tgg tgg      534
Ala Trp Ile His Leu Ser Arg Glu Leu Gly Ile Thr Ile Lys Trp Trp
    155                 160                 165 agc cca act act aca ccg aat agt ccc gat gat cca gtt ctg acg act      582
Ser Pro Thr Thr Thr Pro Asn Ser Pro Asp Asp Pro Val Leu Thr Thr
170                 175                 180                 185 gac tca ttg aag ccc ttg ctt agt cca aaa acg cgc ctt gtt aca tgt      630
Asp Ser Leu Lys Pro Leu Leu Ser Pro Lys Thr Arg Leu Val Thr Cys
                190                 195                 200 aat cac gtg tcg aat gtt gta gga acc atc cac cct att cgt gag att      678
Asn His Val Ser Asn Val Val Gly Thr Ile His Pro Ile Arg Glu Ile
            205                 210                 215 gcc gac gtg gta cat acc att cct gga tgc atg ctt atc gtt gac ggt      726
Ala Asp Val Val His Thr Ile Pro Gly Cys Met Leu Ile Val Asp Gly
        220                 225                 230 gtg gca tgt gtc ccg cat cgt cca gtt gat gtt aaa gaa ttg gat gta      774
Val Ala Cys Val Pro His Arg Pro Val Asp Val Lys Glu Leu Asp Val
    235                 240                 245 gat ttt tac tgc ttt tcc tgg tac aag ttg ttc gga ccg cat ctt gga      822
Asp Phe Tyr Cys Phe Ser Trp Tyr Lys Leu Phe Gly Pro His Leu Gly
250                 255                 260                 265 acc ctg tat gct tcc cgc aaa gcc caa gac cgc tat atg acc tca att      870
Thr Leu Tyr Ala Ser Arg Lys Ala Gln Asp Arg Tyr Met Thr Ser Ile
                270                 275                 280 aac cat tac ttc gtc tca tcg tcg agc ctt gat ggt aag ctg gca tta      918
Asn His Tyr Phe Val Ser Ser Ser Ser Leu Asp Gly Lys Leu Ala Leu
            285                 290                 295 ggc atg ccg tcc ttt gaa ctg cag ttg atg tgc tct cca att gtt tcg      966
Gly Met Pro Ser Phe Glu Leu Gln Leu Met Cys Ser Pro Ile Val Ser
        300                 305                 310 tat ttg caa gat acg gtg ggc tgg gac cgt atc gtg cgc caa gag act     1014
Tyr Leu Gln Asp Thr Val Gly Trp Asp Arg Ile Val Arg Gln Glu Thr
    315                 320                 325 gtg ctg gta act att ttg ttg gag tat tta ctt agc aag cca tct gta     1062
Val Leu Val Thr Ile Leu Leu Glu Tyr Leu Leu Ser Lys Pro Ser Val
330                 335                 340                 345
```

```
tat cgt gtg ttc gga cgt cgt aat tct gat ccc agt cag cgt gta gca      1110
Tyr Arg Val Phe Gly Arg Arg Asn Ser Asp Pro Ser Gln Arg Val Ala
        350                 355                 360 atc gta act ttt gaa gtc gtg gga cgt agt tcc ggg gat gtg gca atg      1158
Ile Val Thr Phe Glu Val Val Gly Arg Ser Ser Gly Asp Val Ala Met
        365                 370                 375 cgc gta aat acg cgt aat cgc ttc cgc att acc tct gga att tgc ctg      1206
Arg Val Asn Thr Arg Asn Arg Phe Arg Ile Thr Ser Gly Ile Cys Leu
        380                 385                 390 gca ccg cgc ccg aca tgg gac gtc ttg aaa ccg aag agt agc gac gga      1254
Ala Pro Arg Pro Thr Trp Asp Val Leu Lys Pro Lys Ser Ser Asp Gly
        395                 400                 405 ctt gtt cgc gtc agc ttt gta cat tac aac acg gtt gag gaa gtg cgt      1302
Leu Val Arg Val Ser Phe Val His Tyr Asn Thr Val Glu Glu Val Arg
410                 415                 420                 425 gcg ttc tgc agc gag tta gac gag att gtg aca cgc gac acc ctc gag      1350
Ala Phe Cys Ser Glu Leu Asp Glu Ile Val Thr Arg Asp Thr Leu Glu
                430                 435                 440 cac cat cac cat cac cat tgagatccgg ctgc                              1382
His His His His His His
                445
```

<210> SEQ ID NO 3
<211> LENGTH: 447
<212> TYPE: PRT
<213> ORGANISM: Aspergillus flavus

<400> SEQUENCE: 3

```
Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
        115                 120                 125

Leu Ser Leu Lys Pro Met Leu Asn Asn Asp Cys Glu Ile Val Cys Ser
    130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
    210                 215                 220
```

```
Pro Gly Cys Met Leu Ile Val Asp Gly Val Ala Cys Val Pro His Arg
225                 230                 235                 240

Pro Val Asp Val Lys Glu Leu Val Asp Phe Tyr Cys Phe Ser Trp
            245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
        290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
                340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
370                 375                 380

Phe Arg Ile Thr Ser Gly Ile Cys Leu Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr Leu Glu His His His His His His
            435                 440                 445

<210> SEQ ID NO 4
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 4

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
        115                 120                 125

Leu Ser Leu Lys Pro Met Leu Asn Asn Asp Cys Glu Ile Val Cys Ser
    130                 135                 140
```

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Thr Pro Asn
            165                 170                 175

Ser Pro Asp Asp Pro Val Leu Thr Thr Asp Ser Leu Lys Pro Leu Leu
        180                 185                 190

Ser Pro Lys Thr Arg Leu Val Thr Cys Asn His Val Ser Asn Val Val
    195                 200                 205

Gly Thr Ile His Pro Ile Arg Glu Ile Ala Asp Val Val His Thr Ile
210                 215                 220

Pro Gly Cys Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350

Asn Ser Asp Pro Ser Gln Arg Val Ala Ile Val Thr Phe Glu Val Val
        355                 360                 365

Gly Arg Ser Ser Gly Asp Val Ala Met Arg Val Asn Thr Arg Asn Arg
    370                 375                 380

Phe Arg Ile Thr Ser Gly Ile Leu Leu Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435

<210> SEQ ID NO 5
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 5

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

```
Leu Lys Glu Ala Ile Glu Ser Thr Ser Asn Phe Met Tyr Ser Phe Pro
 65                  70                  75                  80

Phe Pro Pro Gly Val Asp Ala Lys Ser Met Glu Ala Ile Thr Ala Tyr
                 85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
            115                 120                 125

Leu Ser Leu Lys Pro Met Leu Asn Asn Asp Cys Glu Ile Val Cys Ser
        130                 135                 140

Thr Leu Cys His Glu Ala Ala Ala Ser Ala Trp Ile His Leu Ser Arg
145                 150                 155                 160

Glu Leu Gly Ile Thr Ile Lys Trp Trp Ser Pro Thr Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
210                 215                 220

Pro Gly Cys Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350

Asn Ser Asp Pro Ser Gln Arg Val Ala Ile Val Thr Phe Glu Val Val
        355                 360                 365

Gly Arg Ser Ser Gly Asp Val Ala Met Arg Val Asn Thr Arg Asn Arg
370                 375                 380

Phe Arg Ile Thr Ser Gly Ile Cys Met Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435
```

<210> SEQ ID NO 6
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 6

```
Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
        115                 120                 125

Leu Ser Leu Lys Pro Met Leu Asn Asn Asp Cys Glu Ile Val Cys Ser
    130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
    210                 215                 220

Pro Gly Cys Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350

Asn Ser Asp Pro Ser Gln Arg Val Ala Ile Val Thr Phe Glu Val Val
        355                 360                 365

Gly Arg Ser Ser Gly Asp Val Ala Met Arg Val Asn Thr Arg Asn Arg
    370                 375                 380

Phe Arg Ile Thr Ser Gly Ile Leu Met Ala Pro Arg Pro Thr Trp Asp
385                 390                 395                 400

Val Leu Lys Pro Lys Ser Ser Asp Gly Leu Val Arg Val Ser Phe Val
```

```
                    405                 410                 415
His Tyr Asn Thr Val Glu Glu Val Arg Ala Phe Cys Ser Glu Leu Asp
                420                 425                 430

Glu Ile Val Thr Arg Asp Thr
            435

<210> SEQ ID NO 7
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 7

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Cys Leu Phe Arg Leu Leu Gly
        115                 120                 125

Leu Ser Leu Lys Pro Met Leu Asn Asn Asp Cys Glu Ile Val Cys Ser
130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
    210                 215                 220

Pro Gly Cys Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
```

```
                    325                 330                 335
Glu Tyr Leu Leu Ser Lys Pro Ser Val Tyr Arg Val Phe Gly Arg Arg
                340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
        370                 375                 380

Phe Arg Ile Thr Ser Gly Phe Val Phe Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435

<210> SEQ ID NO 8
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 8

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val

```
                        245                 250                 255
Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
            275                 280                 285

Ser Ser Leu Asp Gly Lys Leu Ala Leu Gly Met Pro Ser Phe Glu Leu
            290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
370                 375                 380

Phe Arg Ile Thr Ser Gly Thr Leu Met Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435

<210> SEQ ID NO 9
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 9

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
            35                  40                  45

Leu Gly Gly Glu Thr Ala Ala Phe Asn Asn Ala Ser Gly Thr Val Val
            50                  55                  60

Leu Lys Glu Ala Ile Glu Ser Thr Ser Asn Phe Met Tyr Ser Phe Pro
65              70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Ala Leu Phe Arg Leu Leu Gly
            115                 120                 125

Leu Ser Leu Lys Pro Met Leu Asn Asn Asp Cys Glu Ile Val Cys Ser
            130                 135                 140

Thr Leu Cys His Glu Ala Ala Ala Ser Ala Trp Ile His Leu Ser Arg
145                 150                 155                 160

Glu Leu Gly Ile Thr Ile Lys Trp Trp Ser Pro Thr Thr Thr Pro Asn
```

-continued

```
                165                 170                 175
Ser Pro Asp Asp Pro Val Leu Thr Thr Asp Ser Leu Lys Pro Leu Leu
            180                 185                 190
Ser Pro Lys Thr Arg Leu Val Thr Cys Asn His Val Ser Asn Val Val
        195                 200                 205
Gly Thr Ile His Pro Ile Arg Glu Ile Ala Asp Val His Thr Ile
    210                 215                 220
Pro Gly Ala Met Leu Ile Val Asp Gly Val Ala Ser Val Pro His Arg
225                 230                 235                 240
Pro Val Asp Val Lys Glu Leu Asp Val Asp Phe Tyr Cys Phe Ser Trp
                245                 250                 255
Tyr Lys Leu Phe Gly Pro His Leu Gly Thr Leu Tyr Ala Ser Arg Lys
            260                 265                 270
Ala Gln Asp Arg Tyr Met Thr Ser Ile Asn His Tyr Phe Val Ser Ser
        275                 280                 285
Ser Ser Leu Asp Gly Lys Leu Ala Leu Gly Met Pro Ser Phe Glu Leu
    290                 295                 300
Gln Leu Met Cys Ser Pro Ile Val Ser Tyr Leu Gln Asp Thr Val Gly
305                 310                 315                 320
Trp Asp Arg Ile Val Arg Gln Glu Thr Val Leu Val Thr Ile Leu Leu
                325                 330                 335
Glu Tyr Leu Leu Ser Lys Pro Ser Val Tyr Arg Val Phe Gly Arg Arg
            340                 345                 350
Asn Ser Asp Pro Ser Gln Arg Val Ala Ile Val Thr Phe Glu Val Val
        355                 360                 365
Gly Arg Ser Ser Gly Asp Val Ala Met Arg Val Asn Thr Arg Asn Arg
    370                 375                 380
Phe Arg Ile Thr Ser Gly Thr Leu Met Ala Pro Arg Pro Thr Trp Asp
385                 390                 395                 400
Val Leu Lys Pro Lys Ser Ser Asp Gly Leu Val Arg Val Ser Phe Val
                405                 410                 415
His Tyr Asn Thr Val Glu Glu Val Arg Ala Phe Cys Ser Glu Leu Asp
            420                 425                 430
Glu Ile Val Thr Arg Asp Thr
            435

<210> SEQ ID NO 10
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 10

Met Lys Ser Val Ala Thr Ser Ser Leu Asp Asp Val Asp Lys Asp Ser
1               5                   10                  15
Val Pro Leu Gly Ser Ser Ile Asn Gly Thr Ala Gln Ala Glu Thr Pro

```
                        85                  90                  95
Thr Gly Asn Lys Gly Lys Val Ala Ala Phe Ile Asn Ala Leu Pro Asp
                100                 105                 110
Glu Ile Thr Phe Gly Gln Ser Thr Thr Ala Leu Phe Arg Leu Leu Gly
            115                 120                 125
Leu Ser Leu Lys Pro Met Leu Asn Asn Asp Ser Glu Ile Val Cys Ser
        130                 135                 140
Thr Leu Cys His Glu Ala Ala Ala Ser Ala Trp Ile His Leu Ser Arg
145                 150                 155                 160
Glu Leu Gly Ile Thr Ile Lys Trp Trp Ser Pro Thr Thr Pro Asn
                165                 170                 175
Ser Pro Asp Asp Pro Val Leu Thr Thr Asp Ser Leu Lys Pro Leu Leu
                180                 185                 190
Ser Pro Lys Thr Arg Leu Val Thr Cys Asn His Val Ser Asn Val Val
                195                 200                 205
Gly Thr Ile His Pro Ile Arg Glu Ile Ala Asp Val Val His Thr Ile
            210                 215                 220
Pro Gly Cys Met Leu Ile Val Asp Gly Val Ala Ser Val Pro His Arg
225                 230                 235                 240
Pro Val Asp Val Lys Glu Leu Asp Val Asp Phe Tyr Cys Phe Ser Trp
                245                 250                 255
Tyr Lys Leu Phe Gly Pro His Leu Gly Thr Leu Tyr Ala Ser Arg Lys
                260                 265                 270
Ala Gln Asp Arg Tyr Met Thr Ser Ile Asn His Tyr Phe Val Ser Ser
                275                 280                 285
Ser Ser Leu Asp Gly Lys Leu Ala Leu Gly Met Pro Ser Phe Glu Leu
        290                 295                 300
Gln Leu Met Cys Ser Pro Ile Val Ser Tyr Leu Gln Asp Thr Val Gly
305                 310                 315                 320
Trp Asp Arg Ile Val Arg Gln Glu Thr Val Leu Val Thr Ile Leu Leu
                325                 330                 335
Glu Tyr Leu Leu Ser Lys Pro Ser Val Tyr Arg Val Phe Gly Arg Arg
            340                 345                 350
Asn Ser Asp Pro Ser Gln Arg Val Ala Ile Val Thr Phe Glu Val Val
        355                 360                 365
Gly Arg Ser Ser Gly Asp Val Ala Met Arg Val Asn Thr Arg Asn Arg
    370                 375                 380
Phe Arg Ile Thr Ser Gly Thr Leu Met Ala Pro Arg Pro Thr Trp Asp
385                 390                 395                 400
Val Leu Lys Pro Lys Ser Ser Asp Gly Leu Val Arg Val Ser Phe Val
                405                 410                 415
His Tyr Asn Thr Val Glu Glu Val Arg Ala Phe Cys Ser Glu Leu Asp
            420                 425                 430
Glu Ile Val Thr Arg Asp Thr
            435

<210> SEQ ID NO 11
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 11

Met Lys Ser Val Ala Thr Ser Ser Leu Asp Asp Val Asp Lys Asp Ser
```

```
  1               5                  10                 15
Val Pro Leu Gly Ser Ser Ile Asn Gly Thr Ala Gln Ala Glu Thr Pro
                20                 25                 30

Leu Glu Asn Val Ile Asp Val Glu Ser Val Arg Ser His Phe Pro Val
                35                 40                 45

Leu Gly Gly Glu Thr Ala Ala Phe Asn Asn Ala Ser Gly Thr Val Val
                50                 55                 60

Leu Lys Glu Ala Ile Glu Ser Thr Ser Asn Phe Met Tyr Ser Phe Pro
 65                 70                 75                 80

Phe Pro Pro Gly Val Asp Ala Lys Ser Met Glu Ala Ile Thr Ala Tyr
                85                 90                 95

Thr Gly Asn Lys Gly Lys Val Ala Ala Phe Ile Asn Ala Leu Pro Asp
               100                105                110

Glu Ile Thr Phe Gly Gln Ser Thr Thr Ala Leu Phe Arg Leu Leu Gly
               115                120                125

Leu Ser Leu Lys Pro Met Leu Asn Asn Asp Ser Glu Ile Val Cys Ser
130                135                140

Thr Leu Cys His Glu Ala Ala Ser Ala Trp Ile His Leu Ser Arg
145                150                155                160

Glu Leu Gly Ile Thr Ile Lys Trp Trp Ser Pro Thr Thr Pro Asn
               165                170                175

Ser Pro Asp Asp Pro Val Leu Thr Thr Asp Ser Leu Lys Pro Leu Leu
               180                185                190

Ser Pro Lys Thr Arg Leu Val Thr Cys Asn His Val Ser Asn Val Val
               195                200                205

Gly Thr Ile His Pro Ile Arg Glu Ile Ala Asp Val Val His Thr Ile
               210                215                220

Pro Gly Ala Met Leu Ile Val Asp Gly Val Ala Ser Val Pro His Arg
225                230                235                240

Pro Val Asp Val Lys Glu Leu Asp Val Asp Phe Tyr Cys Phe Ser Trp
               245                250                255

Tyr Lys Leu Phe Gly Pro His Leu Gly Thr Leu Tyr Ala Ser Arg Lys
               260                265                270

Ala Gln Asp Arg Tyr Met Thr Ser Ile Asn His Tyr Phe Val Ser Ser
               275                280                285

Ser Ser Leu Asp Gly Lys Leu Ala Leu Gly Met Pro Ser Phe Glu Leu
               290                295                300

Gln Leu Met Cys Ser Pro Ile Val Ser Tyr Leu Gln Asp Thr Val Gly
305                310                315                320

Trp Asp Arg Ile Val Arg Gln Glu Thr Val Leu Val Thr Ile Leu Leu
               325                330                335

Glu Tyr Leu Leu Ser Lys Pro Ser Val Tyr Arg Val Phe Gly Arg Arg
               340                345                350

Asn Ser Asp Pro Ser Gln Arg Val Ala Ile Val Thr Phe Glu Val Val
               355                360                365

Gly Arg Ser Ser Gly Asp Val Ala Met Arg Val Asn Thr Arg Asn Arg
               370                375                380

Phe Arg Ile Thr Ser Gly Thr Leu Met Ala Pro Arg Pro Thr Trp Asp
385                390                395                400

Val Leu Lys Pro Lys Ser Ser Asp Gly Leu Val Arg Val Ser Phe Val
               405                410                415

His Tyr Asn Thr Val Glu Glu Val Arg Ala Phe Cys Ser Glu Leu Asp
               420                425                430
```

```
Glu Ile Val Thr Arg Asp Thr
        435

<210> SEQ ID NO 12
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 12

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Ala Leu Phe Arg Leu Leu Gly
        115                 120                 125

Leu Ser Leu Lys Pro Met Leu Asn Asn Asp Ser Glu Ile Val Cys Ser
130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
    210                 215                 220

Pro Gly Ala Met Leu Ile Val Asp Gly Val Ala Cys Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350
```

```
Asn Ser Asp Pro Ser Gln Arg Val Ala Ile Val Thr Phe Glu Val Val
        355                 360                 365

Gly Arg Ser Ser Gly Asp Val Ala Met Arg Val Asn Thr Arg Asn Arg
    370                 375                 380

Phe Arg Ile Thr Ser Gly Thr Leu Met Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435

<210> SEQ ID NO 13
<211> LENGTH: 439
<212> TYPE: PRT
<213> ORGANISM: Artificial Sequence
<220> FEATURE:
<223> OTHER INFORMATION: Unnatural, Mutated UstD Enzyme

<400> SEQUENCE: 13

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80

Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Ser Leu Phe Arg Leu Leu Gly
        115                 120                 125

Leu Ser Leu Lys Pro Met Leu Asn Asn Asp Cys Glu Ile Val Cys Ser
    130                 135                 140

Thr Leu Cys His Glu Ala Ala Ser Ala Trp Ile His Leu Ser Arg
145                 150                 155                 160

Glu Leu Gly Ile Thr Ile Lys Trp Trp Ser Pro Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
        195                 200                 205

Gly Thr Ile His Pro Ile Arg Glu Ile Ala Asp Val Val His Thr Ile
    210                 215                 220

Pro Gly Ala Met Leu Ile Val Asp Gly Val Ala Ser Val Pro His Arg
225                 230                 235                 240

Pro Val Asp Val Lys Glu Leu Asp Val Asp Phe Tyr Cys Phe Ser Trp
                245                 250                 255

Tyr Lys Leu Phe Gly Pro His Leu Gly Thr Leu Tyr Ala Ser Arg Lys
            260                 265                 270
```

```
Ala Gln Asp Arg Tyr Met Thr Ser Ile Asn His Tyr Phe Val Ser Ser
        275                 280                 285

Ser Ser Leu Asp Gly Lys Leu Ala Leu Gly Met Pro Ser Phe Glu Leu
    290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
                340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
370                 375                 380

Phe Arg Ile Thr Ser Gly Thr Leu Met Ala Pro Arg Pro Thr Trp Asp
385                 390                 395                 400

Val Leu Lys Pro Lys Ser Ser Asp Gly Leu Val Arg Val Ser Phe Val
                405                 410                 415

His Tyr Asn Thr Val Glu Glu Val Arg Ala Phe Cys Ser Glu Leu Asp
            420                 425                 430

Glu Ile Val Thr Arg Asp Thr
            435

<210> SEQ ID NO 14
<211> LENGTH: 439
<212> TYPE: PRT
<213> ORGANISM: Artificial Sequence
<220> FEATURE:
<223> OTHER INFORMATION: Unnatural, Mutated UstD Enzyme
<220> FEATURE:
<221> NAME/KEY: MISC_FEATURE
<222> LOCATION: (122)..(122)
<223> OTHER INFORMATION: Xaa at residue 122 may be Ala, Cys, Gly, Phe,
      Ser, or Val
<220> FEATURE:
<221> NAME/KEY: MISC_FEATURE
<222> LOCATION: (139)..(139)
<223> OTHER INFORMATION: Xaa at residue 139 may be Cys or Ser
<220> FEATURE:
<221> NAME/KEY: MISC_FEATURE
<222> LOCATION: (227)..(227)
<223> OTHER INFORMATION: Xaa at residue 227 may be Ala, Cys, Gly, or Ser
<220> FEATURE:
<221> NAME/KEY: MISC_FEATURE
<222> LOCATION: (236)..(236)
<223> OTHER INFORMATION: Xaa at residue 236 may be Cys, Ser, or Trp
<220> FEATURE:
<221> NAME/KEY: MISC_FEATURE
<222> LOCATION: (428)..(428)
<223> OTHER INFORMATION: Xaa at residue 428 may be Ala, Cys, Gly, or Ser

<400> SEQUENCE: 14

Met Lys Ser Val Ala Thr Ser Ser Leu Asp Asp Val Asp Lys Asp Ser
1               5                   10                  15

Val Pro Leu Gly Ser Ser Ile Asn Gly Thr Ala Gln Ala Glu Thr Pro
            20                  25                  30

Leu Glu Asn Val Ile Asp Val Glu Ser Val Arg Ser His Phe Pro Val
        35                  40                  45

Leu Gly Gly Glu Thr Ala Ala Phe Asn Asn Ala Ser Gly Thr Val Val
    50                  55                  60

Leu Lys Glu Ala Ile Glu Ser Thr Ser Asn Phe Met Tyr Ser Phe Pro
65                  70                  75                  80
```

```
Phe Pro Pro Gly Val Asp Ala Lys Ser Met Glu Ala Ile Thr Ala Tyr
                85                  90                  95

Thr Gly Asn Lys Gly Lys Val Ala Ala Phe Ile Asn Ala Leu Pro Asp
            100                 105                 110

Glu Ile Thr Phe Gly Gln Ser Thr Thr Xaa Leu Phe Arg Leu Leu Gly
            115                 120                 125

Leu Ser Leu Lys Pro Met Leu Asn Asn Asp Xaa Glu Ile Val Cys Ser
130                 135                 140

Thr Leu Cys His Glu Ala Ala Ala Ser Ala Trp Ile His Leu Ser Arg
145                 150                 155                 160

Glu Leu Gly Ile Thr Ile Lys Trp Trp Ser Pro Thr Thr Pro Asn
                165                 170                 175

Ser Pro Asp Asp Pro Val Leu Thr Thr Asp Ser Leu Lys Pro Leu Leu
            180                 185                 190

Ser Pro Lys Thr Arg Leu Val Thr Cys Asn His Val Ser Asn Val Val
            195                 200                 205

Gly Thr Ile His Pro Ile Arg Glu Ile Ala Asp Val Val His Thr Ile
        210                 215                 220

Pro Gly Xaa Met Leu Ile Val Asp Gly Val Ala Xaa Val Pro His Arg
225                 230                 235                 240

Pro Val Asp Val Lys Glu Leu Asp Val Asp Phe Tyr Cys Phe Ser Trp
            245                 250                 255

Tyr Lys Leu Phe Gly Pro His Leu Gly Thr Leu Tyr Ala Ser Arg Lys
            260                 265                 270

Ala Gln Asp Arg Tyr Met Thr Ser Ile Asn His Tyr Phe Val Ser Ser
            275                 280                 285

Ser Ser Leu Asp Gly Lys Leu Ala Leu Gly Met Pro Ser Phe Glu Leu
290                 295                 300

Gln Leu Met Cys Ser Pro Ile Val Ser Tyr Leu Gln Asp Thr Val Gly
305                 310                 315                 320

Trp Asp Arg Ile Val Arg Gln Glu Thr Val Leu Val Thr Ile Leu Leu
                325                 330                 335

Glu Tyr Leu Leu Ser Lys Pro Ser Val Tyr Arg Val Phe Gly Arg Arg
            340                 345                 350

Asn Ser Asp Pro Ser Gln Arg Val Ala Ile Val Thr Phe Glu Val Val
            355                 360                 365

Gly Arg Ser Ser Gly Asp Val Ala Met Arg Val Asn Thr Arg Asn Arg
370                 375                 380

Phe Arg Ile Thr Ser Gly Ile Cys Leu Ala Pro Arg Pro Thr Trp Asp
385                 390                 395                 400

Val Leu Lys Pro Lys Ser Ser Asp Gly Leu Val Arg Val Ser Phe Val
            405                 410                 415

His Tyr Asn Thr Val Glu Glu Val Arg Ala Phe Xaa Ser Glu Leu Asp
            420                 425                 430

Glu Ile Val Thr Arg Asp Thr
            435
```